US006878758B2

(12) United States Patent
Martin et al.

(10) Patent No.: US 6,878,758 B2
(45) Date of Patent: Apr. 12, 2005

(54) POLYHYDROXYALKANOATE COMPOSITIONS HAVING CONTROLLED DEGRADATION RATES

(75) Inventors: David P. Martin, Arlington, MA (US); Frank Skraly, Somerville, MA (US); Simon F. Williams, Sherborn, MA (US)

(73) Assignee: Metabolix, Inc., Cambridge, MA (US)

( * ) Notice: Subject to any disclaimer, the term of this patent is extended or adjusted under 35 U.S.C. 154(b) by 31 days.

(21) Appl. No.: 10/403,942

(22) Filed: Mar. 28, 2003

(65) Prior Publication Data

US 2003/0236320 A1 Dec. 25, 2003

Related U.S. Application Data

(60) Division of application No. 09/218,575, filed on Dec. 22, 1998, now Pat. No. 6,610,764, and a continuation-in-part of application No. 09/076,198, filed on May 12, 1998, now Pat. No. 6,245,537.
(60) Provisional application No. 60/068,455, filed on Dec. 22, 1997, provisional application No. 60/046,211, filed on May 12, 1997, provisional application No. 60/054,289, filed on Jul. 31, 1997, provisional application No. 60/063,501, filed on Oct. 24, 1997, and provisional application No. 60/065,921, filed on Jan. 17, 1997.

(51) Int. Cl.[7] .............................................. C08L 67/04

(52) U.S. Cl. ...................................... 523/124; 525/450

(58) Field of Search .......................... 523/124; 525/450

(56) References Cited

U.S. PATENT DOCUMENTS

| | | | |
|---|---|---|---|
| 3,982,543 A | 9/1976 | Schmitt et al. | |
| 4,648,978 A | 3/1987 | Makinen et al. | |
| 4,711,241 A | 12/1987 | Lehmann | |
| 4,826,493 A | 5/1989 | Martini et al. | |
| 4,880,592 A | 11/1989 | Martini et al. | |
| 4,910,145 A | 3/1990 | Holmes et al. | |
| 5,236,431 A | * 8/1993 | Gogolewski et al. | 606/72 |
| 5,245,023 A | 9/1993 | Peoples et al. | |
| 5,250,430 A | 10/1993 | Peoples et al. | |
| 5,271,961 A | 12/1993 | Mathiowitz et al. | |
| 5,278,256 A | 1/1994 | Bellis | |
| 5,292,860 A | 3/1994 | Shiotani et al. | |
| 5,334,698 A | 8/1994 | Witholt et al. | |
| 5,480,794 A | 1/1996 | Peoples et al. | |
| 5,489,470 A | 2/1996 | Noda | |
| 5,502,116 A | 3/1996 | Noda | |
| 5,502,158 A | 3/1996 | Sinclair et al. | |
| 5,512,669 A | 4/1996 | Peoples et al. | |
| 5,534,432 A | 7/1996 | Peoples et al. | |
| 5,536,564 A | 7/1996 | Noda | |
| 5,563,239 A | 10/1996 | Hubbs et al. | |
| 5,614,576 A | 3/1997 | Rutherford et al. | |
| 5,625,030 A | 4/1997 | Williams et al. | |
| 5,703,160 A | 12/1997 | Dehennua et al. | |
| 5,705,187 A | 1/1998 | Unger | |
| 5,711,933 A | 1/1998 | Bichon et al. | |
| 5,994,478 A | 11/1999 | Asrar et al. | |

FOREIGN PATENT DOCUMENTS

| | | |
|---|---|---|
| DE | 39 37 649 | 5/1991 |
| EP | 0 258 781 | 3/1988 |
| EP | 0 423 484 | 4/1991 |
| EP | 0 601 885 | 6/1994 |
| EP | 0 628 586 | 12/1994 |
| EP | 0 754 467 | 1/1997 |
| JP | 4-326932 | 11/1992 |
| JP | 5-023189 | 2/1993 |
| JP | 7-275344 A | 10/1995 |
| WO | WO 92/18164 | 10/1992 |
| WO | WO 93/20134 | 10/1993 |
| WO | WO 94/06886 | 3/1994 |
| WO | WO 95/03356 | 2/1995 |
| WO | WO 95/03358 | 2/1995 |
| WO | WO 95/20614 | 8/1995 |
| WO | WO 95/20615 | 8/1995 |
| WO | WO 95/20621 | 8/1995 |
| WO | WO 95/23250 | 8/1995 |
| WO | WO 95/33874 | 12/1995 |
| WO | WO 96/00263 | 1/1996 |
| WO | WO 96/08535 | 3/1996 |
| WO | WO 96/18420 | 6/1996 |
| WO | WO 98/04292 | 2/1998 |
| WO | WO 98/39453 | 9/1998 |
| WO | WO 98/51812 | 11/1998 |

OTHER PUBLICATIONS

Agostini, et al., "Synthesis and Characterization of Poly–β–Hydroxybutyrate. I. Synthesis of Crystalline DL Poly–β–Hydroxybutyrate from DL–β–Butyrolactone," *Polym. Sci.* Part A–1 9:2775–87 (1971).

(Continued)

*Primary Examiner*—Peter Szekely
(74) *Attorney, Agent, or Firm*—Pabst Patent Group LLP

(57) ABSTRACT

Biocompatible polyhydroxyalkanoate compositions with controlled degradation rates have been developed. In one embodiment, the polyhydroxyalkanoates contain additives to alter the degradation rates. In another embodiment, the polyhydroxyalkanoates are formed of mixtures of monomers or include pendant groups or modifications in their backbones to alter their degradation rates. In still another embodiment, the polyhydroxyalkanoates are chemically modified. Methods for manufacturing the devices which increase porosity or exposed surface area can be used to alter degradability. For example, as demonstrated by the examples, porous polyhydroxyalkanoates can be made using methods that creates pores, voids, or interstitial spacing, such as an emulsion or spray drying technique, or which incorporate leachable or lyophilizable particles within the polymer. Examples describe poly(4HB) compositions including foams, coatings, meshes, and microparticles. As demonstrated by the examples, these polyhydroxyalkanoate compositions have extremely favorable mechanical properties, as well as are biocompatible and degrade within desirable time frames under physioogical conditions. These polyhydroxyalkanoate materials provide a wider range of polyhydroxyalkanoate degradation rates than are currently available. Methods for processing these materials, particularly for therapeutic, prophylactic or diagnostic applications, or into devices which can be implanted or injected, are also described.

26 Claims, 2 Drawing Sheets

OTHER PUBLICATIONS

Akhtar, "Physiomechanical Properties of bacterial P(HB–HV) Polyesters and Their Uses in drug Delivery," The British Library Document Supply Centre, UMI, (1990).

Anderson, et al., "Occurrence, Metabolism, metabolic Role, and Industrial Uses of bacterial Polyhydroxyalkanoates," *Microbiological Reviews* pp. 450–472 (1990).

Bailey, "Free radical ring–opening polymerization," *J. Polym. Preprints* 25:210–11 (1984).

Bailey, et al., "Synthesis of Poly–ε–caprolactone via a free radical mechanism. Free radical ring–opening polymerization of 2–methylene–1,3–dioxepane," *J. Polym. Sci. Polym. Chem.* 20:3021–30 (1982).

Bruhn & Muller, "Preparation and characterization of spray–dried Poly(DL–Lactide) Micro Spheres," *Proceed. Intern. Symp. Control. Rel. Bioact. Mater.* 18:668–69 (1991).

Byrom, "Miscellaneous Biomaterials" in Biomaterials (D. Byrom, ed.) pp. 333–359 (MacMillan Publishers, London 1991).

Conti, B. et al., "Use of polylactic acid for the preparation of microparticulate drug delivery systems," *J. Microencapsulation* 9:153–166 (1992).

Cookson, "It grows on trees," *Financial Times* p. 6 (Aug. 12, 1992).

De Smet, et al., "Characterization of intracellular inclusions formed by *Pseudomonas oleovorans* during growth on octane," *J. Bacteriol.* 154:870–78 (1983).

DuBois, et al., "Macromolecular Engineering of Polylactones and Polylactides. 12. Study of the Depolymerization Reactions of Poly (ε–caprolactone) with Functional Aluminum Alkoxide End Groups," *Macromolecules* 26:4407–12 (1993).

Duvernoy, et al., "A biodegradable patch used as a pericardial substitute after cardiac surgery: 6– and 24–month evaluation with CT," *Thorac. Cardiovasc. Surg.* 43(5):271–74 (1995).

Fukuzaki, et al., "Direct copolymerization of L–lactic acid with γ–butyrolactone in the absence of catalysis," *Die Madromoleculare Chemie* 190:1553–59 (1989).

Gagnon, et al., "A thermoplastic elastomer produced by the bacterium *Pseudomonas oleovarans*," *Rubber World* 207:32–38 (1992).

Gagnon, et al., "Chemical modification of bacterial elastomers: 1. Peroxide crosslinking," *Polymer* 35:4358–67 (1994).

Gerngross & Martin, "Enzyme–catalyzed synthesis of poly [(R)–(–)–3–hydroxybutyrate]: formation of macroscopic granules in vivo," *Proc. Natl. Acad. Sci. USA* 92:6279–83 (1995).

Gross, et al., "Polymerization of β–Monosubstituted–β–propiolactones Using Trialkylaluminum–Water Catalytic Systems and Polymer Characterization," *Macromolecules* 21:2657–68 (1988).

Hein, et al., "Biosynthesis of poly(4–hydroxybutyric acid) by recombinant strains of *Escherichia coli.*, " *FEMS Microbiol. Lett.* 153:411–18 (1997).

Hocking & Marchessault, "Syndiotactic poly[(R, S)–β–hydroxybutyrate] isolated from methyaluminoxane–catalyzed polymerization," *Polym. Bull.* 30:163–70 (1993).

Hocking & Marchessault, "Biopolyesters" in *Chemistry and Technology of Biodegradable Polymers*, (G.J.L. Griffin, ed.), pp. 48–96, Chapman and Hall: London, 1994.

Holmes, "Biologically Produced (R)–3–hydroxyalkanoate Polymers and Copolymers," in *Developments in Crystalline Polymers* (Bassett, ed.), pp. 1–65, Elsevier, London: 1988.

Hori, et al., "Chemical synthesis of high molecular weight poly (3–hydroxybutyrate–co–4–hydroxybutyrate)," *Polymer* 36:4703–05 (1996).

Hori, et al., "Ring Opening Copolymerization of Optically Active β–Butyrolactone with Several Lactones Catalyzed by Distannoxane Complexes: Synthesis of New Biodegradable Polyesters," *Macromolecules* 26:4388–90 (1993).

Hori, et al., "Ring–Opening Polymerization of Optically Active β–Butyrolactone Using Distannoxane Catalysts: Synthesis of High Molecular Wright Poly(3–hydroxybutyrate)," *Macromolecules* 26:5533–34 (1993).

Horsch, "Inheritance of Functional Foreign Genes in Plants" *Science* 223: 49–498 (1984).

Hutmacher, et al., "A review of material properties of biodegradable and bioresorbable polymers and devices for GTR and GBR applications," *Int. J. Oral Maxillofac. Implants* 11(5):667–78 (1996).

Keeler, "Don't Let Food Go To Waste—Make Plastic Out of It," *R&D Magazine* pp. 52–57 (1991).

Keeler, "Plastics Grown in Bacteria Inch Toward the Market," *R&D Magazine* pp. 48–52 (1991).

Kemnitzer, et al., "Preparation of predominantly Syndiotactic Poly(β–hydroxybutyrate) by the Tributylin Methoxide Catalyzed Ring–Opening Polymerization of racemic β–Butyrolactone," *Macromolecules* 26:1221–29 (1983).

Kishida, et al., "Formulation–assisted biodegradable polymer matrices," *Pharmaceutical Society of Japan* 37:1954–56 (1989).

Koosha, "Preparation and characterization of biodegradable polymeric drug carriers," Ph.D. Dissertation, 1989, Univ. Nottingham, UK., *Diss. Abstr. Int.* B51:1206 (1990).

Koosha, et al., "Polyhydroxybutyrate as a drug carrier," *Crit. Rev. Ther. Drug Carrier Syst.* 6(2): 117–30 (1989).

Korte & Gelt, "Hochdruckreactionen. II. Die Polymerisation Von γ butyrolacton und δ–valerolactam bei hohen drücken," *Polymer Lett.* 4:685–89 (1966).

Kusaka, et al., "Microbial synthesis and Physical Properties of ultra–high–molecular–weight poly [(R)–3–hydroxybutyrate]," *Pure Appl. Chem.* A35:319–35 (1998).

Lafferty, et al., "Microbial Production of Poly–65 –hydroxybutyric acid" in *Biotechnology* (H.J. Rehm and G. Reed, eds.), Verlagsgesellschaft, Weinheim, vol. 66, pp. 135–176 (1988).

Le Borgne & Spassky, "Stereoelective polymerization of β–butyrolactone," *Polymer* 30:2312–19 (1989).

Lee, et al., "Copolymerization of γ–butyrolactone and β–butyrolactone," *Macromol. Chem. Phys.* 198:1109–20 (1997).

Lemoigne & Roukhelman, "Fermentation β–Hydroxybutyrique Caracterisation of Evolution Des Produits de Deshydration et de Polymerisation de L'acide β–Dehydroxybutyrique," *Annales des fermentations,* 5:527–36 (1925).

Lloyd, et al., "Transformation of *Arabidopsis thalania* with *Agrobacterium tumefaciens,*" *Science* 234: 464–66 (1986).

Malm, et al., "A new biodegradable patch for closure of atrial septal defect. An experimental study," *Scand. J. Thorac. Cardiovasc. Surg.* 26(1):9–14 (1992).

Malm, et al., "Enlargement of the right ventricular outflow tract and the pulmonary artery with a new biodegradable patch in transannular position," *Eur. Surg. Res.* 26(5):298–308 (1994).

Malm, et al., "Prevention of postoperative pericardial adhesions by closure of the pericardium with absorbable polymer patches. An experimental study," *J. Thorac. Cardiovasc. Surg.* 104(3):600–07 (1992).

Mathiowitz & Langer, "Polyanhydride microspheres as drug delivery systems" in *Microcapsules Nanopart. Med. Pharm.* (Donbrow, ed.), pp. 99–123 (CRC:Boca Raton, Florida, 1992).

Maysinger, "Microencapsulation and the Grafting of Genetically Transformed Cells as Therapeutic Strategies to rescue Degenerating Neurons of the CNS," *Reviews in the Neurosciences,* 6:15–33 (1995).

McMillin, "Elastomers for Biomedical Applications," *Rubber Chem. Technol.* 67:417–48 (1994).

McWilliams, "Plastics as High as An Elephant's Eye?" *Business Week* pp. 110–111 (1991).

Müller, et al., "Poly(hydroxyalkanoates): A Fifth Class of Physiologically Important Organic Biopolymers," *Angew Chem. Int. Ed. Engl.* 32: 477–502 (1993).

Nakamura, et al., "Microbial synthesis and characterization of poly(3–hydroxybutyrate–co–4–hydroxybutyrate)," *Macromol.* 25:4237–4241 (1992).

Nobes, et al., "Polyhydroxyalkanoates: Materials for delivery systems," *Drug. Del.* 5:167–77 (1998).

Ogawa, Y. et al., "A New Technique to Efficiently Entrap Leuprolide Acetate in Microcapsules of Poly Lactic Acid or Copoly(lactic/Glycolic) Acid," *Chem. Pharm. Bull.* 36:1095–103 (1988).

Otera, et al., "Distannoxane as reverse micelle–type catalyst: novel solvent effect on reaction rate of transesterification," *J. Org. Chem.* 54:4013–14 (1989).

Otera, et al., "Distannoxane–catalysed transesterification of 1,n–Dioldiacetates. Selective transformation of either of chemically equivalent functional groups," *J. Chem. Soc. Chem. Commun.* 1742–43 (1991).

Otera, et al., "Novel distannoxane–catalyzed transesterification and a new entry to α,β–unsaturated carboxylic acids," *Tetrahedron Lett.,* 27:2383–86 (1986).

Otera, et al., "Novel template effects of distannoxanne catalysts in highly efficient transesterification and esterification," *J. Org. Chem.* 56:5307–11 (1991).

Peoples, et al., "Poly–β–hydroxybutyrate Biosynthesis in *Alcaligenes eutrophus* H16," *J. Biol. Chem* 264(26):15293–97 (1989).

Peoples, et al., "Polyhydroxybutyrate (PHB): A Model System for Biopolymer Engineering: II," in *Novel Biodegradable Microbial Polymers,* (Dawes, ed.) pp. 191–202, Kluwer Academic Publishers:Netherlands (1990).

Poirier, "Perspectives on the production of polyhydroxyalkanoate in plants," *FEMS Microbiology Reviews* 103:237–46 (1992).

Poirier, et al., "Progress Toward Biologically Produced Biodegradable thermoplastics," *Adv. Mater.* 5(1):30–37 (1993).

Pool, "In Search of the Plastic Potato," *Science* 245: 1187–89 (1989).

Pouton & Akhtar, "Biosynthetic polyhydroxyalkanoates and their potential in drug delivery," *Adv. Drug Delivery Rev.* 18:133–62 (1996).

Rivard, et al., "Fibroblast seeding and culture in biodegradable porous substrates," *J. Appl. Biomater.* 6(1):65–68 (1995).

Saito, et al., "Microbial synthesis and properties of poly(3–hydroxybutyrate–co–4–hydroxybutyrate) in *Comamonas acidovorans,*" *Int. J. Biol. Macromol.* 16(2):99–104 (1994).

Schwartz & Goodman, *Plastic Materials and Processes,* (Van Nostrand Reinhold Company:New York, 1982).

Sim, et al., "PHA synthase activity controls the molecular weight and polydispersity of polyhydroxybutyrate in vivo," *Nat. Biotechnol.* 15(1):63–67 (1997).

Stanton & Gagne, "The remarkable catalytic activity of alkali–metal alkoxide clusters in the ester interchange reaction," *J. Am. Chem. Soc.* 119:5075–76 (1997).

Steinbuchel & Valentin, "Diversity of bacterial polyhydroxyalkanoic acids," *FEMS Microbiol. Lett.* 128:219–28 (1995).

Steinbuchel & Wiese, "A Pseudomonas strain accumulating polyesters of 3–hydroxybutyric acid and medium–chain–length 3–hydroxyalkanoic acids," *Appl. Microbiol. Biotechnol.* 37:691–97 (1992).

Steinbuchel, "Polyhydroxyalkanoic Acids" in *Biomaterials* (Byrom, ed.), pp. 123–213 (MacMillan Publishers:London 1991).

Steinbuchel, et al., "Molecular basis for biosynthesis and accumulation of polyhydroxyalkanoic acids in bacteria," *FEMS Microbiology Reviews* 103: 217–30 (1992).

Tanahashi & Doi, "Thermal Properties of Stereoregularity of Poly(3–hydroxybutyrate) Prepared from optically Active B–Butyrolactone with a Zinc–Based Catalyst," *Macromolecules* 24:5732–33 (1991).

Valentin, et al., "Identification of 5–hydroxyhexanoic acid, 4–hydroxyaheptanoic acid and 4–hydroxyoctanoic acid as new constituents of bacterial polyhydroxyalkanoic acids," *Appl. Microbiol. Biotechnol.* 46:261–87 (1996).

Valentin, et al., "Identification of (4–hydroxyhexanoic acid as a new constituent of biosynthetic polyhydroxyalkanoic acids from bacteria," *Appl. Microbiol. Biotechnol.* 40:710–716 (1994).

Wallen & Rowedder, "Poly–β–hydroxyalakaonate from Activated Sludge," *Environ. Sci. Technol.* 8:578–79 (1974).

Williams & Peoples, "Biodegradable plastics from plants," *CHEMTECH* 26:38–44 (1996).

Williams, et al., "Making plastics green," *Chem. Br.* 33:29–32 (1997).

Xie, et al., "Ring–opening Polymerization of β–butyrolactone by Thermophilic Lipases," *Macromolecules* 30:6997–98 (1997).

\* cited by examiner

POLYHYDROXYALKANOATE COMPOSITIONS HAVING CONTROLLED DEGRADATION RATES

FIELD OF THE INVENTION

The present invention generally relates to polyhydroxyalkanoate polymers and methods for altering their rates of degradation, particularly methods which accelerate this process, and novel biodegradable polyhydroxyalkanoates which are particularly suited for medical applications.

This application is a divisional of U.S. Ser. No. 09/218,575 filed Dec. 22, 1998, which issued as U.S. Pat. No. 6,610,764 on Aug. 26, 2003 entitled *Polyhydroxyalkanoate Compositions Having Controlled Degradation*", by David P. Martin, Frank Skraly, and Simon F. Williams, which claims priority to provisional application U.S. Ser. No. 60/068,455, entitled "*Methods for Altering The Degradation of Polyhydroxyalkanoates*" filed Dec. 22, 1997 by Simon F. Williams and David P. Martin, and is also a continuation-in-part of U.S. Ser. No. 09/076,198, which issued as U.S. Pat. No. 6.245.537 on Jun. 12, 2001, entitled "*Polyhydroxyalkanoates for In Vivo Applications*" by Williams et al., filed May 12, 1998, which claims priority to U.S. Ser. No. 60/046,211, entitled "*Biocompatible Polyhydroxyalkanoates*" filed May 12, 1997 by Simon F. Williams; Ser. No. 60/054,289, entitled "*Derivatization of PHAs for Biomedical Applications*" filed Jul. 31, 1997 by David Martin; Ser. No. 60/063,501, entitled "*Polyhydroxy Alkanoate Stents*" filed Oct. 24, 1997 by Simon F. Williams and David P. Martin; and Ser. No. 60/065,921, entitled "*Methods for Making Biocompatible Polyhydroxyalkanoates*" filed Nov. 17, 1997 by Simon F. Williams and David P. Martin.

BACKGROUND OF THE INVENTION

In the medical area, a number of degradable polymers have been developed that breakdown in vivo into their respective monomers within weeks or a few months. Despite the availability of these synthetic degradable polymers, there is still a need to develop degradable polymers which can further extend the range of available options. In particular there is a need to develop degradable polymers which offer a wider range of mechanical properties.

Polyhydroxyalkanoates are natural, thermoplastic polyesters and can be processed by traditional polymer techniques for use in an enormous variety of applications, including consumer packaging, disposable diaper linings and garbage bags, food and medical products. Initial efforts focused on molding applications, in particular for consumer packaging items such as bottles, cosmetic containers, pens, golf tees and the like. U.S. Pat. Nos. 4,826,493 and 4,880,592 describe the manufacture of PHB and PHBV films and their use as diaper backsheet. U.S. Pat. No. 5,292,860 describes the manufacture of the PHA copolymer poly(3-hydroxybutyrate-co-3-hydroxyhexanoate) and the use of these polymers for making diaper backsheet film and other disposable items. Diaper back sheet materials and other materials for manufacturing biodegradable or compostable personal hygiene articles from PHB copolymers other than PHBV are described in PCT WO 95/20614, WO 95/20621, WO 95/23250 WO 95/20615, WO 95/33874, U.S. Pat. No. 5,502,116, U.S. Pat. No. 5,536,564, U.S. Pat. No. 5,489,470 and WO 96/08535.

One of the most useful properties of PHAs which readily distinguishes them from petrochemical derived polymers is their biodegradability. Produced naturally by soil bacteria, the PHAs are degraded upon subsequent exposure to these same bacteria in either soil, compost, or marine sediment. Biodegradation of PHAs is dependent upon a number of factors such as the microbial activity of the environment and the surface area of the item. In addition, temperature, pH, molecular weight and crystallinity are important factors. Biodegradation starts when microorganisms begin growing on the surface of the plastic and secrete enzymes which break down the polymer into hydroxy acid monomeric units. The hydroxy acids are then taken up by the microorganisms and used as carbon sources for growth. In aerobic environments the polymers are degraded to carbon dioxide and water, whereas in anaerobic environments the degradation products are carbon dioxide and methane (Williams, S. F. and Peoples, O. P., *CHEMTECH*, 26, 38–44 (1996)). While the mechanism for degradation of PHAs in the environment is widely considered to be via enzymatic attack and can be relatively rapid, the mechanism of degradation in vivo is generally understood to involve simple hydrolytic attack on the polymers' ester linkages. It may or may not be protein mediated. Unlike polymers comprising 2-hydroxyacids like polyglycolic and polylactic acid, the polyhydroxyalkanoates are normally comprised of 3-hydroxyacids and in certain cases even 4,5, and 6-hydroxyacids. Ester linkages derived from these hydroxyacids are generally less susceptible to hydrolysis than ester linkages derived from 2-hydroxyacids.

Researchers have developed processes for the production of a great variety of PHAs and around 100 different monomers have been incorporated into polymers under controlled fermentation conditions (Steinbütchel, A. and Valentin, H. E., *FEMS Microbiol., Lett.,* 128:219–228 (1995)). There are currently only two commercially available PHA compositions, poly-(R)-3-hydroxybutyrate (PHB) and poly-(R)-3-hydroxybutyrate-co-(R)-3-hydroxyvalerate (PHBV). Because of their great compositional diversity, PHAs with a range of physical properties can be produced (Williams, S. F. and Peoples, O. P., *CHEMTECH*, 26:38–44 (1996)). The commercially available PHAs, PHB and PHBV, represent only a small component of the property sets available to the PHAs. For example, the extension to break of PHB and PHBV range from around 4 to 42%, whereas the same property for poly-4-hydroxybutyrate (P4HB) is about 1000% (Saito, Y. and Doi, Y. *Int. J. Biol. Macromol.* (1994) 16: 99–104). Similarly, the values of Young's modulus and tensile strength for PHB and PHBV are 3.5 to 0.5 GPa and 40 to 16 MPa, respectively (for increasing HV content to 25 mol %), compared to 149 MPa and 104 MPa, respectively for P4HB (Saito, Y. and Doi, Y. *Int. J. Biol. Macromol.* (1994) 16: 99–104).

In addition to finding commercial use as a biodegradable replacement for synthetic commodity resins, PHB and PHBV have been extensively studied for use in biomedical applications. These studies range from potential uses in controlled release which have been reviewed by Koosha, F. et al., *Crit. Rev. Ther. Drug Carrier Syst.* 6:117–130 (1989) and Pouton C. W. and Akhtar, S. *Adv. Drug Delivery Rev.,* 18:133–162 (1996), to use in formulation of tablets, surgical sutures, wound dressings, lubricating powders, blood vessels, tissue scaffolds, surgical implants to join tubular body parts, bone fracture fixation plates, and other orthopedic uses, as described in WO 98/51812 by Metabolix. Perhaps the most advanced medical development is the use of PHB and PHBV for preparing a porous, bioresorbable flexible sheet for tissue separation and stimulation of tissue regeneration in injured soft tissue described in European Patent Application 754 467 A1 to Bowald, S. and Johansson-Ruden, G. filed Jun. 26, 1988 and EP 0349505 A2. Recent reports have also described the use of PHBV to sustain cell growth (Rivard, C. H. et al., *J. Appl. Biomat.,* 6:65–68 (1995)).

Besides biocompatibility, it is often desired that an implanted medical device should degrade after its primary function has been met. PHB and PHBV, the only PHAs tested as medical implants to date, have shown very long in vivo degradation periods, of greater than one year for PHB (Duvernoy, O., Malm, et al. *Thorac. Cardiovasc. Surgeon* (1995) 43: 271–74. Malm, et al., C. J. *Thorac. Cardiovasc. Surg.* (1992) 104: 600–607.). For many applications, this very long degradation time is undesirable as the persistence of polymer at a wound healing site may lead to a chronic inflammatory response in the patient. Slowly degrading PHB patches used to regenerate arterial tissue have been found to elicit a long term (greater than two years) macrophage response (Malm, et al.,. *Eur. Surg. Res.* 1994, 26: 298–308). Macrophages were identified as being involved in the degradation of the PHB implants and this long term macrophage response appears to indicate the presence of persistent, slowly degrading particulate material originating from the implant. Indeed, although a PHB patch used for repair of the pericardium was not seen by ordinary light microscopy after 12 months implantation, small residual particulate material was observed by polarized light microscopy (Malm, et al., C. *Scand. J. Thor. Cardiovasc. Surg.* 1992, 26; 9–14). It is not clear if this particulate material remains localized at the implant site, or may migrate throughout the body, causing unforeseen complications. The biological fate, or medical impact of this particulate material, cannot be predicted without long term study. In order to minimize potential problems associated with slowly degrading PHAs, it is advantageous to utilize resorbable materials with faster in vivo degradation rates.

There has been only one report describing the biocompatibility or in vivo degradation of any other PHA polymer in biomedical applications (WO 98/51812). U.S. Pat. No. 5,334,698 to Witholt, B. and Lageveen, R. G. mentions medical articles manufactured with an optically active polyester isolated from *Pseudomonas oleovorans* cells, however, no examples or discussion of fabrication or biocompatibility testing are cited, and no methods are provided to obtain the polymer in a suitably pure form for in vivo medical use. Since bacteria suitable for production of these polymers may also produce an endotoxin as well as other inflammatory mediators, it is important that the polymer be processed to remove these contaminants. For many applications, the rate of PHA biodegradation is well suited to the required product lifetime. However, in certain cases it would be desirable to be able to exert more control over the rate at which the polymers breakdown in the environment. Such control would extend the range of applications for this class of polymers. For example, a PHA film may have suitable mechanical properties to be used as a mulch film, yet not have the most optimum rate of degradation for the application. The ability to be able to control the rate of degradation of the polymer in the environment would thus be a distinct advantage.

Thus while the polyhydroxyalkanoates offer a wide range of mechanical properties which are potentially useful in medical applications, their use particularly in vivo as resorbable polymers has been limited by their slow hydrolysis. It would thus be desirable to develop methods for controlling the rates of degradation of polyhydroxyalkanoates.

It is therefore an object of this invention to provide methods for controlling the rates of degradation of polyhydroxyalkanoates.

It is further object of this invention to provide new compositions comprising or derived from polyhydroxyalkanoates which degrade more readily in the environment and/or in vivo.

It is another object of this invention to provide methods for fabricating articles and devices from these compositions.

SUMMARY OF THE INVENTION

Biocompatible polyhydroxyalkanoate compositions with controlled degradation rates have been developed. In one embodiment, the polyhydroxyalkanoates contain additives to alter the degradation rates. In another embodiment, the polyhydroxyalkanoates are formed of mixtures of monomers or include pendant groups or modifications in their backbones to alter their degradation rates. In still another embodiment, the polyhydroxyalkanoates are chemically modified. Methods for manufacturing the devices which increase porosity or exposed surface area can be used to alter degradability. For example, as demonstrated by the examples, porous polyhydroxyalkanoates can be made using methods that creates pores, voids, or interstitial spacing, such as an emulsion or spray drying technique, or which incorporate leachable or lyophilizable particles within the polymer. Examples describe poly(4HB) compositions including foams, coatings, meshes, and microparticles. As demonstrated by the examples, these polyhydroxyalkanoate compositions have extremely favorable mechanical properties, as well as are biocompatible and degrade within desirable time frames under physioogical conditions. These polyhydroxyalkanoate materials provide a wider range of polyhydroxyalkanoate degradation rates than are currently available.

Methods for processing these materials, particularly for therapeutic, prophylactic or diagnostic applications, or into devices which can be implanted or injected, are also described.

DETAILED DESCRIPTION OF THE INVENTION

I. PHA COMPOSITIONS

Polymer Compositions

As used herein, "PHA materials" contain one or more units, for example between 10 and 100,000, and preferably between 100 and 30,000 units of the following formula I:

wherein n is an integer, for example between 1 and 15, and in a preferred embodiment, between 1 and 4; and wherein $R^1$, $R^2$, $R^3$, and $R^4$ independently can be hydrocarbon radicals including long chain hydrocarbon radicals; halo- and hydroxy-substituted radicals; hydroxy radicals; halogen radicals; nitrogen-substituted radicals; oxygen-substituted radicals; and/or hydrogen atoms.

As used herein, the formula —$(CR^3R^4)_n$— is defined as including the following formulas:

—$CR^3R^4$-(where n=1);

—$CR^3R^4CR^{3'}R^{4'}$-(where n=2); and

—$CR^3R^4CR^{3'}R^{4'}CR^{3''}R^{4''}$-(where n=3);

wherein $R^3$, $R^4$, $R^{3'}$, $R^{4'}$, $R^{3''}$, and $R^{4''}$ can be independently hydrocarbon radicals including long chain hydrocarbon radicals; halo- and hydroxy-substituted radicals; hydroxy radicals; halogen radicals; nitrogen-substituted radicals; oxygen-substituted radicals; and/or hydrogen atoms. Thus, formula I includes units derived from 3-hydroxyacids (n=1), 4-hydroxyacids (n=2), and 5-hydroxyacids (n=3).

These units may be the same in a homopolymer, or be more different units, as for example in a copolymer or terpolymer. The polymers typically have a molecular weight over 300, for example between 300 and $10^7$, and in a preferred embodiment 10,000 to 10,000,000 Daltons.

The PHA materials may contain or be modified to include other molecules, such as bioactive and detectable compounds, surface active agents, other degradable or non-degradable polymers, as well as materials used to modify the mechanical properties of PHAs such as plasticizers, fillers, nucleating agents, colorants, stabilizers, modifiers and binders.

Representative PHAs which can be modified or formulated as described herein are described in: Steinbüchel, A. and Valentin, H. E., *FEMS Microbiol., Lett.*, 128:219–228 (1995).

PHB and P4HB possess very different physical properties. A range of PHA copolymers containing 4-hydroxybutyrate are either known or can be prepared with a range of intermediate properties between those of PHB and P4HB (Saito, Y. and Doi, Y. Int. J. Biol. Macromol. (1994) 16: 99–104), however, biomedical applications, biocompatibility testing and in vivo degradation of P4HB and its copolymers have not been reported. PHA copolymers of 4HB and 3HB varying in composition from 0 to 100% 4HB have been produced in *Alcaligenes eutrophus* (Nakamura, S., Doi, Y. and Scandola, M. *Macromol.* (1992) 25:4237–4231) and from 64 to 100% 4HB in *Comamonas acidovorans* (Saito, Y. and Doi, Y. *Int. J. Biol. Macromol.* (1994) 16: 99–104), however, these polymers were of modest molecular mass ($1 \times 10^5$ to $5 \times 10^5$ g/mol, by GPC) compared to the molecular mass produced in recombinant *E. coli* (greater than $5 \times 10^5$ g/mol, GPC).

Figure 1:
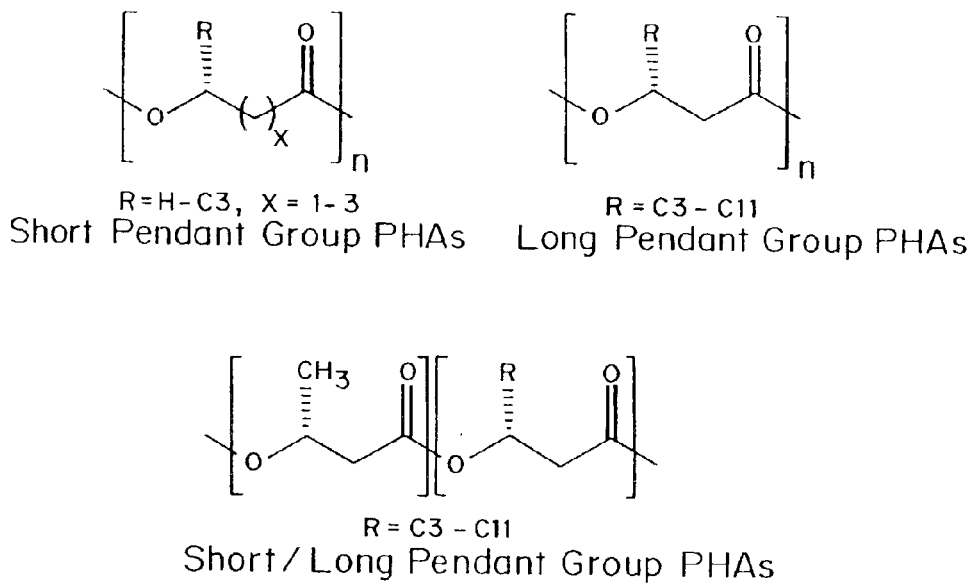
FIG. 1 is a schematic of PHA biopolymers broadly divided into groups according to the length of their pendant groups and their respective biosynthetic pathways.

The PHA biopolymers may be broadly divided into three groups according to the length of their pendant groups and their respective biosynthetic pathways (FIG. 1). Those with short pendant groups, such as polyhydroxybutyrate (PHB), a homopolymer of R-3-hydroxybutyric acid (R-3HB) units, are highly crystalline thermoplastic materials, and have been known the longest (Lemoigne, M. and Roukhelman, N., *Annales des fermentations*, 5:527–536 (1925)). A second group of PHAs containing the short R-3HB units randomly polymerized with much longer pendant group hydroxy acid units were first reported in the early seventies (Wallen, L. L. and Rohwedder, W. K., *Environ. Sci. Technol.*, 8:576–579 (1974)). A number of microorganisms which specifically produce copolymers of R-3HB with these longer pendant group hydroxy acid units are also known and belong to this second group (Steinbüchel, A. and Wiese, S., *Appl. Microbiol. Biotechnol.*, 37:691–697 (1992)). In the early eighties, a research group in The Netherlands identified a third group of PHAs, which contained predominantly longer pendant group hydroxy acids (De Smet, M. J. et al., *J. Bacteriol.*, 154:870–878 (1983)).

Figure 2A:
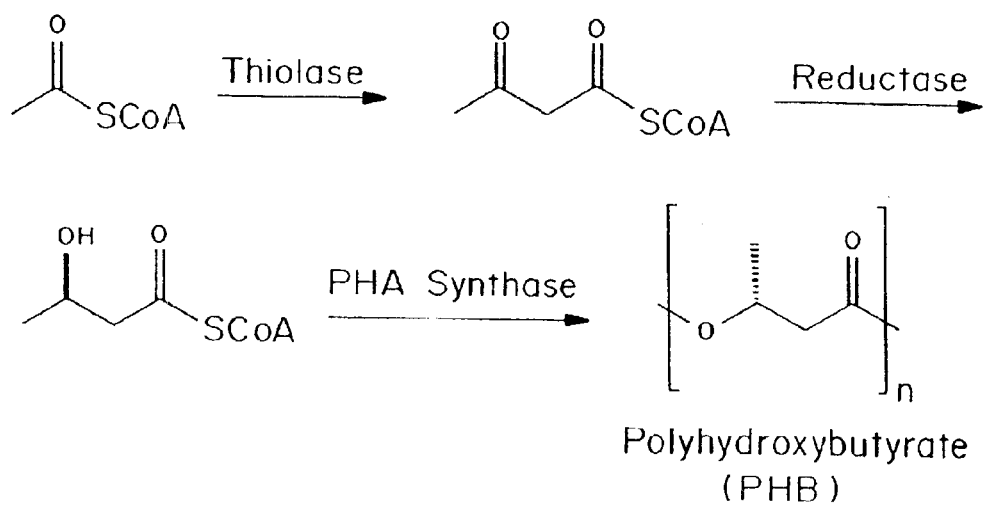
FIG. 2*a* is a schematic of the pathways by which short pendant group PHAs are derived.
Figure 2B:
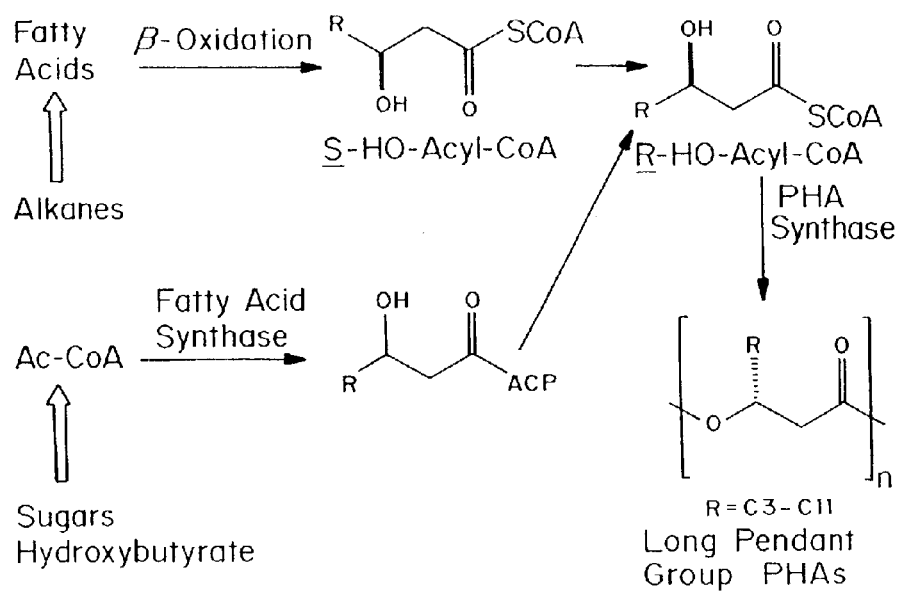
FIG. 2*b* is a schematic of the pathways by which long pendant group PHAs are derived.

The PHA polymers may constitute up to 90% of the dry cell weight of bacteria, and are found as discrete granules inside the bacterial cells. These PHA granules accumulate in response to nutrient limitation and serve as carbon and energy reserve materials. Distinct pathways are used by microorganisms to produce each group of these polymers. One of these pathways leading to the short pendant group polyhydroxyalkanoates (SPGPHAs) involves three enzymes, namely thiolase, reductase and PHB synthase (sometimes called polymerase). Using this pathway, the homopolymer PHB is synthesized by condensation of two molecules of acetyl-Coenzyme A to give acetoacetyl-Coenzyme A, followed by reduction of this intermediate to R-3-hydroxybutyryl-Coenzyme A, and subsequent polymerization (FIG. 2a). The last enzyme in this pathway, the synthase, has a substrate specificity that can accommodate C3–C5 monomeric units including R-4-hydroxy acid and R-5-hydroxy acid units. This biosynthetic pathway is found, for example, in the bacteria *Zoogloea ramigera* and *Alcaligenes eutrophus*. The biosynthetic pathway which is used to make the third group of PHAs, the long pendant group polyhydroxyalkanoates (LPGPHAs) is still partly unknown, however, it is currently thought that the monomeric hydroxyacyl units leading to the LPGPHAs are derived by the b-oxidation of fatty acids and the fatty acid pathway (FIG. 2b). The R-3-hydroxyacyl-Coenzyme substrates resulting from these routes are then polymerized by PHA synthases (sometimes called polymerases) that have substrate specificities favoring the larger monomeric units in the C6–C14 range. Long pendant group PHAs are produced, for example, by *Pseudomonads*.

Presumably, the second group of PHAs containing both short R-3HB units and longer pendant group monomers utilize both the pathways shown in FIGS. 2a and 2b to provide the hydroxy acid monomers. The latter are then polymerized by PHA synthases able to accept these units.

In all, about 100 different types of hydroxy acids have been incorporated into PHAs by fermentation methods (Steinbichel, A. and Valentin, H. E., *FEMS Microbiol., Lett.*, 128:219–228 (1995)). Notably, these include PHAs containing functionalized pendant groups such as esters, double bonds, alkoxy, aromatic, halogens and hydroxy groups.

A preferred polyhydroxyalkanoate for medical applications is P4HB. P4HB is biocompatible, resorbable, processable, strong and ductile. Maintenance of breaking strength is another very important parameter for suturing and stapling materials, especially resorbable ones. As resorbable materials are degraded in vivo, their physical and mechanical properties change as the result of this degradation. For instance, a resorbable suture will loose most of its breaking strength, and as such its ability to fix tissue, more rapidly than the time for its complete resorption. PGA sutures, for example, will loose most of their strength within three weeks in vivo (Vet Surg 21;192:355–61), but not be completely resorbed before six weeks. This loss of mechanical strength is the result of molecular mass decrease of the polymer. It is important to note that a number of parameters will affect resorption rates and suture breaking strength in vivo, such as type of tissue, mechanical stresses, presence of infection, etc.

The examples demonstrate that the degradation rate of P4HB in vivo is fast relative to other PHAs, however, its resorption rate is slower than many of the materials used as resorbable sutures. Additionally, as shown in Table 7, P4HB implants maintain their molecular mass during the process of resorption. This maintenance of molecular mass is expected to be a benefit for the maintenance of mechanical properties, and as such breaking strength of PHAs used as wound closing materials. Because of their excellent mechanical properties, maintenance of high molecular mass, processability, biocompatibility and resorbability, P4HB and P4HB-co-HA should be useful as resorbable wound closure materials such as suturing and stapling materials, particularly as modified herein to increase their degradation rates.

Sources of PHAs

PHA materials which can be modified to alter their degradation rates can be derived from either a biological source, an enzymatic source, or a chemical source. The biological source can be a microorganism or higher organism such as a plant, and can be derived by genetic engineering.

During the mid-1980's, several research groups were actively identifying and isolating the genes and gene products responsible for PHA synthesis. These efforts lead to the development of transgenic systems for production of PHAs in both microorganism and plants, as well as enzymatic methods for PHA synthesis. Such routes could increase further the available PHA types. These advances have been reviewed in Williams, S. F. and Peoples, O. P., *CHEMTECH*, 26, 38–44 (1996), and Williams S. F. and Peoples, O. P., *Chem. Br.* 33, 29–32 (1997).

Methods which can be used for producing PHA polymers suitable for subsequent modification to alter their rates of degradation are described in: U.S. Pat. No. 4,910,145 to Holmes, P. A. and Lim, G. B.; Byrom, D., "Miscellaneous Biomaterials," in D. Byrom, Ed., "Biomaterials" MacMillan Publishers, London, 1991, pp. 333–359; Hocking, P. J. and Marchessault, R. H. "Biopolyesters", G. J. L. Griffin, Ed., "Chemistry and Technology of Biodegradable Polymers," Chapman and Hall, London, 1994, pp.48–96; Holmes, P. A., "Biologically Produced (R)-3-hydroxyalkanoate Polymers and Copolymers," in D. C. Bassett Ed., "Developments in Crystalline Polymers," Elsevier, London, Vol. 2, 1988, pp. 1–65; Lafferty et al., "Microbial Production of Poly-b-hydroxybutyric acid," H. J. Rehm and G. Reed, Eds., "Biotechnology", Verlagsgesellschaft, Weinheim, Vol. 66, 1988, pp. 135–176; Müller and Seebach, *Angew. Chem. Int. Ed. Engl.* 32:477–502 (1993); Steinbüchel, A. "Polyhydroxyalkanoic Acids," in D. Byrom Ed., "Biomaterials", MacMillan Publishers, London, 1991, pp. 123–213; and, Williams and Peoples, *CHEMTECH*, 26:38–44, (1996); Steinbüchel and Wiese, *Appl. Microbiol. Biotechnol.*, 37:691–697 (1992); U.S. Pat. Nos. 5,245,023; 5,250,430; 5,480,794; 5,512,669; 5,534,432; Agostini, D. E. et al., *Polym. Sci.*, Part A-1, 9:2775–2787 (1971); Gross, R. A. et al., *Macromolecules*, 21:2657–2668 (1988); Dubois, P. I. et al., *Macromolecules*, 26:4407–4412 (1993); Le Borgne, A. and Spassky, N., *Polymer*, 30:2312–2319 (1989); Tanahashi, N. and Doi, Y., *Macromolecules*, 24:5732–5733 (1991); Hori, Y. M. et al., *Macromolecules*, 26:4388–4390 (1993); Kemnitzer, J. E. et al., *Macromolecules*, 26:1221–1229 (1993); Hori, Y. M. et al., *Macromolecules*, 26:5533–5534 (1993); Hocking, P. J. and Marchessault, R. H., *Polym. Bull.*, 30:163–170 (1993); Xie, W. et al., *Macromolecules*, 30:6997–6998 (1997), and, U.S. Pat. No. 5,563,239 to Hubbs, J. C. and Harrison, M. N. The PHAs derived from these methods may be in any form, including a latex or solid form.

Identification, cloning and expression of the genes involved in the biosynthesis of PHAs from several microorganisms within recombinant organisms allow for the production of PHAs within organisms that are not native PHA producers. Such recombinant organisms provide researchers with a greater degree of control of the PHA production process because they are free of background enzyme activities for the biosynthesis of unwanted PHA precursors or degradation of the PHA. Additionally, the proper selection of a recombinant organism may facilitate purification of, or allow for increased biocompatibility of, the produced PHA.

The minimal requirements for the synthesis of PHA in a recombinant organism are a source of hydroxyalkanoyl-CoA and an appropriate PHA synthase (Gerngross, T. U. and Martin, D. P. *Proc. Natl. Acad. Sci.* (1995) 92: 6279–6283.). Recombinant PHA producers, thus require a biosynthetic pathway for a hydroxyalkanoyl-CoA monomer and a suitable PHA synthase. Production of a homopolymer requires that the organism produce only one suitable substrate for the PHA synthase, as production of multiple substrates results in the formation of a PHA copolymer. Recombinant organisms containing a transgene encoding a PHA synthase are sufficient for production of P4HB.

In the absence of PHA degradation pathways, the molecular mass of the PHA accumulated in recombinant organisms can be very high. PHB produced in recombinant *E. coli* has been reported to have molecular mass of $4 \times 10^6$ g/mol (Sim, S. J., Snell, K. D., Hogan, S. A., Stubbe, J., Rha, C. and Sinskey, A. Nature Biotech. (1997) 15: 63–67). The molecular mass is important for controlling the physical properties of a given PHA, because the increased molecular mass of PHAs produced in recombinant organisms can lead to improved material properties, such as increased tensile strength and ultimate elongation (Kusaka, S., Iwata, T. and Doi, Y. *J.M.S. Pure Appl. Chem.* (1998) A35:319–335).

The biosynthesis of P3HB-co-4HB containing a low level of 4HB (1.5%) has been described in recombinant *E. coli* (Valentin, H. E., Dennis, D. J. *Biotech.* 1997, 58; 33–38). It is noteworthy that the molecular mass of these PHAs were very high (greater than $1 \times 10^6$ g/mol). Additionally, the biosynthesis of the P3HB-co-4HB and the homopolymer P4HB in recombinant *E. coli* have been described (Hein,et al. *FEMS Microbiol. Lett.* 1997, 153; 411–418).

In addition to using biological routes for PHA synthesis, PHA polymers may also be derived by chemical synthesis. One widely used approach involves the ring-opening polymerization of β-lactone monomers using various catalysts or initiators such as aluminoxanes, distannoxanes, or alkoxyzinc and alkoxy-aluminum compounds (see Agostini, D. E. et al., *Polym. Sci.*, Part A-1, 9:2775–2787 (1971); Gross, R. A. et al., *Macromolecules*, 21:2657–2668 (1988); Dubois, P. I. et al., *Macromolecules*, 26:4407–4412 (1993); Le Borgne, A. and Spassky, N., *Polymer*, 30:2312–2319 (1989); Tanahashi, N. and Doi, Y., *Macromolecules*, 24:5732–5733 (1991); Hori, Y. M. et al., *Macromolecules*, 26:4388–4390 (1993); Kemnitzer, J. E. et al., *Macromolecules*, 26:1221–1229 (1993); Hori, Y. M. et al., *Macromolecules*, 26:5533–5534 (1993); Hocking, P. J. and Marchessault, R. H., *Polym. Bull.*, 30:163–170 (1993). A second approach involves condensation polymerization of esters and is described in U.S. Pat. No. 5,563,239 to Hubbs, J. C. and Harrison, M. N., and references therein. Researchers have also developed chemo-enzymatic methods to prepare PHAs. Xie et al., *Macromolecules*, 30:6997–6998 (1997), for example, have reported a ring opening polymerization of beta-butyrolactone by thermophilic lipases to yield PHB.

Biological production of P4HB or P4HB-co-HA has certain advantages over traditional chemical synthetic methods.

The chemical synthesis of high molecular mass P4HB (greater than $1\times10^5$ g/mol) is difficult due to the tendency of the free acid to lactonize to form the relatively unstrained and kinetically favored five-membered ring. Thus, polycondensation of 4-hydroxybutyric acid is difficult to achieve, while the material that results from high pressure ring-opening polymerization reactions of γ-butyrolactone is of very low molecular mass (Korte, F. and Gelt, W. *Polymer Lett.* 1966, 4, 685) and would have poor mechanical properties. An alternate synthetic strategy for P4HB, the free radical ring-opening polymerization of 2-methylene dioxolane, results in a copolymer containing ring opened and unopened units (Bailey,et al. *J. Polym. Sci. Polym. Chem.* (1982) 20: 3021–30. Bailey, W. *J. Polym. Preprints* (1984) 25:210–11.). 4HB has been successfully co-polymerized with 3HB via ring-opening polymerization (Hori, Y., Yamaguchi, A. and Hagiwara, T. *Polymer* 1996, 36, 4703–4705.), however, the molecular weight of the copolymers was modest (less than $1\times10^5$ g/mol), especially for compositions with more than 80% 4HB (less than $2\times10^4$ g/mol). Additionally, many of the catalysts used for the chemical synthesis of polyesters contain toxic metals. These toxic contaminants can be avoided using a biological process to produce PHAs.

II. PHA Formulations Having Altered Degradation Rates

The degradation rates of the polymers can be manipulated through addition of various components to the polymeric composition, as well as selection of the chemical composition, molecular weight, processing conditions, and form of the final polymeric product. The chemical composition can be altered through selection of monomers which are incorporated into the polymer, by alteration of the linkages, chemical backbone or pendant groups, and/or by manipulation of the molecular weight. Increasing porosity, inclusion of hydrophilic substances, and/or increasing surface area exposed to water, will all increase the rate of degradation. Hydrophobic coatings or incorporation into or blended with of hydrophobic substances with the polymers will decrease the rate of degradation.

Additives Altering Degradation Rates

The hydrolysis of polyhydroxyalkanoates is accelerated at acidic or basic pH's and thus the inclusion of acidic or basic additives or excipients can be used to modulate the rate of degradation of PHAs. The excipients can be added as particulates, can be mixed with any other additive or agent incorporated or to be incorporated, or can be dissolved within the polymer. Additives which enhance the rate of degradation include inorganic acids such as ammonium sulfate and ammonium chloride, organic acids such as citric acid, benzoic acids, peptides, ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween™ and Pluronic™. Such additives are preferably used at concentrations between 0.1 and 30% by weight.

The rate of degradation may also be enhanced by additives which form pores or otherwise increase the surface area in the polymer or increase the amorphous content of the polymer. Pore forming agents are generally added as particulates and include water soluble compounds such as inorganic salts and sugars which are removed by leaching. Suitable particles include salt crystals, proteins such as gelatin and agarose, starches, polysaccharides such as alginate and other polymers. The diameters of the particles may suitably be between nanometers to 500 microns. They may also be lyophilizable. Pore forming agents can be included in an amount of between 0.01% and 90% weight to volume, preferably at a level between one and thirty percent (w/w, polymer), to increase pore formation. For example, in spray drying or solvent evaporation, a pore forming agent such as a volatile salt, for example, ammonium bicarbonate, ammonium acetate, ammonium chloride or ammonium benzoate or other lyophilizable salt, is first dissolved in water. The solution containing the pore forming agent is then emulsified with the polymer solution to create droplets of the pore forming agent in the polymer. This emulsion is then spray dried or taken through a solvent evaporation/extraction process. After the polymer is precipitated, the hardened microparticles are frozen and lyophilized to remove the pore forming agents. Plasticizers, such as the citrate esters, and other polymers like atactic polyhydroxyalkanoates, may be added to increase the polymer's amorphous character.

Hydrophobic coatings or materials which can be incorporated to increase the degradation rates include hydrophobic compounds such as phospholipids, cholesterol, and other polymers, as well as surfactants. These materials and methods for forming coatings or incorporation into the materials are described in WO 96/18420 by Bracco Research SA, WO 92/18164 by Delta Biotechnology, Ltd., WO 95/03356 by Massachusetts Institute of Technology, PCT/US97/03007 by Acusphere, U.S. Pat. No. 5,271,961 to Mathiowitz, et al., U.S. Pat. No. 5,711,933 to Bichon, et al., and U.S. Pat. No. 5,705,187 to Unger. Specific examples disclose fatty acids and phospholipids as emulsifiers to stabilize the oil phase in the aqueous phase during emuslion/encapsulation process, with the result that the microspheres arecoated with an outer layer of the surfactant. The use of additives such as fats, waxes, and high molecular weight hydrocarbon are also disclosed to hydrophobize the polymer walls and to slow water penetration.

Modification of PHA Pendant Groups

An alternative method to alter the rate of degradation of PHA polymers involves modification of the polyhydroxyalkanoate pendant groups. The pendant groups may be modified in whole or in part. Pendant groups can, for example, be converted to acidic and basic groups, such as carboxylic acids and amines. These types of groups can enhance degradation by altering local pH values. Alternatively, the pendant groups can be converted to reactive groups, such as alcohols and amines, which can cleave the polymer backbone either by an intramolecular or intermolecular reaction. In addition to these conversions, the pendant groups may also be converted to hydrophilic groups to increase uptake of hydrolytic agents such as water, or they may be converted to groups which would increase the amorphous nature of the polymers. The procedures required to carry out functional group conversion of the pendant groups are well known to those skilled in the art. One suitable method that can be used for preparing a PHA of the invention (incorporating a unit that alters the degradation rate of the polymer) is taught in WO 98/39453 by Hein, Sohling, Gottschalk, and Steinbuchel. Suitable pendant groups in PHA polymers which will alter the rate of degradation can also be derived directly by fermentation.

Chemical Modification of PHAs

The rate of hydrolysis of a polyhydroxyalkanoate depends upon a number of factors. One key factor is the chemical nature or reactivity of the ester linkages between the monomers. The rate of degradation of the PHA backbone can thus be altered by incorporating into the polymer backbone chemical linkages which are more susceptible to hydrolysis, or enzymatic attack. Examples of monomers which can be incorporated into polyhydroxyalkanoate backbones to alter the rate of degradation of the polymer are 2-hydroxy acids, such as glycolic acid and lactic acid, and other hydroxyacids which modulate the reactivity of the ester linkage, such as 2-hydroxyethoxy acetic acid. Besides incorporating other hydroxyacids which yield esters which are more susceptible to hydrolytic or enzymatic attack, other types of functionality may be incorporated into the polymer backbone. For example, one or more of the ester linkages can be replaced by groups such as amide, anhydride, carbonate, or carbamate. Examples of monomers which can be incorporated into the polyhydroxyalkanoate backbone are aminoacids and aminoalcohols. Moreover, multifunctional monomers can be incorporated into the polyhydroxyalkanoate backbones, for example, triols or tetraols. These types of monomer units can also be used to increase or maintain molecular weight of the polymer by interchain crosslinking, or modify crystallinity of the polymers.

A variety of methods may be used to incorporate susceptible chemical linkages into the polyhydroxyalkanoate backbones. For example, co-feeds may be added during fermentation of PHAs which result in the incorporation of desired monomers. Suitable co-feeds include hydroxyalkoxy acetic acids. These types of monomers may also be incorporated during chemical synthesis from hydroxyacid monomers using catalysts, and via coenzyme A derivatives using enzymatic catalysts such as the PHA synthases.

Susceptible chemical linkages may also be incorporated into polyhydroxyalkanoate backbones after their initial synthesis. Methods to accomplish this include chemical transformations such as insertion reactions, irradiation, esterification, transesterification (see for example, Otera, J. et al., *Tetrahedron Lett.*, 27:2383–2386 (1986), Otera J. et al., *J. Org. Chem.*, 56: 5307–5311 (1991), Otera, J. et al., *J. Org. Chem.*, 54:4013–4014 (1989) and Otera, J. et al., *J. Chem. Soc., Chem. Commun.*, 1742–1743 (1991)), ester metathesis reactions (see for example, Stanton, M. G. and Gagné, M. R., *J. Am. Chem. Soc.*, 119:5075–5076 (1997) and references therein), and reactive blending. In the latter case, chemical reactions can be carried out in the melt with a catalyst present. For example, esters or polyesters can be melted with polyhydroxyalkanoates in the presence of suitable catalysts in order to chemically modify the polyhydroxyalkanoate.

Processing of PHAs Including Susceptible Linkages

The polyhydroxyalkanoates may be further manipulated using a wide range of polymer processing techniques. Preferred methods for processing these materials include: solvent casting, melt processing, fiber processing/spinning/weaving, extrusion, injection and compression molding, and lamination.

III. Methods for Manufacturing Medical Devices

The polymer compositions are useful for preparing a variety of biodegradable medical devices. The biodegradable polymers preferably exhibit a relatively slow biodegradation, for example, having a in vivo half-life of between three and six months or less. The polymers preferably have a relatively low melting point/glass transition temperature, for example, less than 136° C., and/or are soluble in a non-toxic, non-halogenated solvent, for ease of processing.

When the depyrogenated PHAs are implanted in the body, these materials show very little, if any, acute inflammatory reaction or any adverse tissue reaction. There is no significant inflammatory response or scar tissue formation. Recruitment of inflammatory cells is minimal. Histological examination of the explanted devices demonstrates that the materials are essentially inert. Accordingly, devices constructed of PHAs can be implanted with minimal adverse affect on the surrounding tissue. Release of the hydroxy acid degradation products from the implanted materials typically is slow and well tolerated by the body. Thus, PHAs are expected to maintain their material properties for a matter of months and will eventually degrade to non-toxic materials.

Devices prepared from the PHAs can be used for a wide range of different medical applications. Examples of such applications include controlled release, drug delivery, tissue engineering scaffolds, cell encapsulation; targeted delivery, biocompatible coatings; biocompatible implants; guided tissue regeneration, wound dressings, orthopedic devices, prosthetics and bone cements (including adhesives and/or structural fillers), and diagnostics.

The PHAs can encapsulate, be mixed with, or be ionically or covalently coupled to any of a variety of therapeutic, prophylactic or diagnostic agents. A wide variety of biologically active materials can be encapsulated or incorporated, either for delivery to a site by the polyhydroxyalkanoate, or to impart properties to the polymer, such as bioadhesion, cell attachment, enhancement of cell growth, inhibition of bacterial growth, and prevention of clot formation.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. The polymer can also be used to encapsulate cells and tissues. Representative diagnostic agents are agents detectable by x-ray, fluorescence, magnetic resonance imaging, radioactivity, ultrasound, computer tomagraphy (CT) and positron emission tomagraphy (PET). Ultrasound diagnostic agents are typically a gas such as air, oxygen or perfluorocarbons.

In the case of controlled release, a wide range of different bioactive compounds can be incorporated into a controlled release device. These include hydrophobic, hydrophilic, and high molecular weight macromolecules such as proteins. The bioactive compound can be incorporated into the PHAs in a percent loading of between 0.1% and 70% by weight, more preferably between 5% and 50% by weight. The PHAs may be in almost any physical form, such as a powder, film, molded item, particles, spheres, latexes, and crystalline or amorphous materials. They can be combined with additional non-PHA materials, for example, other polymers. They are suitable for use in applications requiring slowly degrading, biocompatible, moldable materials, for example, medical devices. Examples of medical devices which can be prepared from the polymers include rods, bone screws, pins, surgical sutures, stents, tissue engineering devices, drug delivery devices, wound dressings, and patches such as hernial patches and pericardial patches.

Degradable implants fabricated with the PHAs may be used in a wide range of orthopedic and vascular applications, tissue engineering, guided tissue regeneration, and applications currently served by other thermoplastic elastomers (McMillin, *Rubber Chem. Technol.*, 67:417–46 (1994)). The implants may include other factors to stimulate repair and healing. Preferred devices are tubes suitable for passage of bodily fluids. These devices may be modified with cell attachment factors, growth factors, peptides, and antibodies and their fragments.

Preferred methods of fabricating medical devices include solvent casting, melt processing, extrusion, injection and compression molding, and spray drying. Particles are preferably prepared directly from a fermentation based process, or by a solvent evaporation technique, double emulsion technique, or by microfluidization, using methods available in the art. (Koosha, F. Ph.D. Dissertation, 1989, Univ. Nottingham, UK., *Diss. Abstr. Int. B* 51:1206 (1990); Bruhn, B. W. and Müeller, B. W. *Proceed. Intern. Symp. Control. Rel. Bioact. Mater.* 18:668–69 (1991); Conti, B. et al., *J. Microencapsulation,* 9:153–166 (1992); Ogawa, Y. et al., *Chem. Pharm. Bull.,* 36:1095–103 (1988); Mathiowitz, E. and Langer, R. "Polyanhydride microspheres as drug delivery systems," M. Donbrow Ed., in *"Microcapsules Nanopart. Med. Pharm."* CRC, Boca Raton, Fla., 1992, Ch. 5, pp. 99–123.)

The PHAs can be fabricated into devices suitable for wound healing. For example, non-woven fibrous materials for this purpose may be prepared from the polymers by first producing polymer fibers, by pressing the polymers through a perforated outlet, using procedures known to those skilled in the art. The fibers can then be fabricated into a porous membrane (cloth) by spreading them on a solid support and subjecting them to compression molding. The thickness of the device is preferably less than 500 $\mu$m. The wound healing device may also be prepared by perforating a film or membrane using a laser to achieve porosity, or using a leaching technique to prepare a porous material. The pore sizes should ideally be small enough to lock out cells and other tissue matter. The wound healing devices may be positioned in vivo to separate tissues and stimulate tissue regeneration.

The PHAs may be used to encapsulate cells. Using procedures known to those skilled in the art, cells first may be pre-coated. Maysinger, *Reviews in the Neurosciences,* 6:15–33 (1995). Using a particle encapsulation procedure such as the double emulsion technique, the cells may then be encapsulated by PHAs. Ogawa, et al., *Chem. Pharm. Bull.,* 36:1095–103 (1988). Encapsulated cells may then be implanted in vivo.

The PHAs may be fabricated into tissue engineering scaffolds using a wide range of polymer processing techniques. Preferred methods of fabricating PHA tissue engineering scaffolds include solvent casting, melt processing, fiber processing/spinning/weaving, extrusion, injection and compression molding, lamination, and solvent leaching/solvent casting. Such methods are known to those skilled in the art.

One preferred method of fabricating a PHA tissue engineering scaffold involves using an extruder, such as a Brabender extruder. For example, this technique can be used to prepare extruded tubes suitable for implantation in a range of lengths and sizes.

Another preferred method involves preparing a nonwoven PHA scaffold from fibers. Fibers may be produced from the melt or solution, and processed into nonwovens using methods known to those skilled in the art. The properties of the nonwoven may be tailored by varying, for example, the PHA material, the fiber dimensions, fiber density, material thickness, fiber orientation, and method of fiber processing. The porous membranes may, if desired, be further processed. For example, these membranes may be formed into hollow tubes.

Another preferred method involves melt or solvent processing a suitable PHA into an appropriate mold and perforating the material using a laser or other means to achieve the desired porosity. Also preferred are methods that include rolling a compression molded PHA sheet into a loop and heat sealing. The PHA sheet optionally may be rolled with another material, such as a second biodegradable polymer. For example, the latter material could be a nonwoven of polyglycolic acid, polylactic acid, or a copolymer of glycolic and lactic acids. Such a procedure should provide a laminated tube suitable for use in the engineering of new vessels, ducts and tubes. The PHAs may also be used to coat other tissue engineering scaffolds. Such materials could be derived from other degradable polymers. Coating may be performed, for example, with a solvent based solution, or by melt techniques, or using a PHA latex.

The tissue engineering devices described herein may be seeded with cells prior to implantation or after implantation. The cells may be harvested from a healthy section of the donor's tissue, expanded in vitro using cell culture techniques, and then seeded into a scaffold (or matrix) either prior to or after implantation. Alternatively, the cells may be obtained from other donor's tissue or from existing cell lines.

The PHAs may be used to coat other devices and materials. Such coatings may improve their properties for medical application, for example, improving their biocompability, mechanical properties, and tailoring their degradation and controlled release profiles. The PHAs may be coated onto other devices using the fabrication procedures described above. The thickness of the coating can be adjusted to the needs of the specific application by changing the coating weight or concentration applied, and/or by overcoating.

The PHAs may be fabricated into stents using a wide range of polymer processing techniques. Preferred methods of fabricating PHA stents include solvent casting, melt processing, fiber processing/spinning, extrusion, injection molding, and compression molding. Such methods are known to those skilled in the art.

Prior to implantation, a bioresorbable polymeric article must be sterilized to prevent disease and infection of the recipient. Sterilization is performed prior to seeding a polymeric device with cells. Heat sterilization of PHA containing articles is often impractical since the heat treatment could deform the article, especially if the PHA has a melting temperature below that required for the heat sterilization treatment. This problem can be overcome using cold ethylene oxide gas as a sterilizing agent. Exposure of a PHA containing article to vapors of ethylene oxide prior to implantation sterilizes the article making it suitable for implantation. During sterilization with cold ethylene oxide gas, the PHA containing article maintains its shape. This type of treatment is ideally suited for sterilization of molded, or pre-formed articles where the shape of the article plays in important role in its proper functioning.

The devices described herein can be administered systemically or locally, or even used in vitro, particularly for cell culture. The preferred methods of systemically administering the devices are by injection, inhalation, oral administration and implantation. Other suitable methods for administering the devices include administering the devices topically, as a lotion, ointment, patch, or dressing.

The compositions and methods described herein will be further understood with reference to the following non-limiting examples.

Example 1

Production of P4HB in Recombinant *Escherichia coli*

E. coli strain MBX1177, a derivative of strain DH5α selected for the ability to grow with 4-hydroxybutyric acid (4HB) as the sole carbon source, was transformed with pFS30, a plasmid containing the genes encoding PHA synthase from *Ralstonia eutropha*, 4-hydroxybutyryl-CoA transferase from *Clostridium kluyveri*, and β-lactamase, which confers resistance to ampicillin. The synthase and transferase are under the control of the trc promoter, which is inducible by isopropyl-β-D-thiogalactopyranoside (IPTG) in pFS30. These cells were first grown in 100 ml LB (Luria Broth, Difco, Detroit, Mich.; 25 g/L) plus 100 μg/ml ampicillin overnight in a 250-ml Erlenmeyer flask at 37° C. with shaking at 200 rpm. This entire culture was used as an inoculum for the fermentation carried out in a 7 L vessel. The first stage of the fermentation consisted of growing biomass in 5 L of LB-ampicillin at 37° C. with stirring at 800 rpm and aeration at 1 volumetric volume of air/min (vvm). After 17 hours, the volume was adjusted to 6 L by adding one liter of medium, such that the total volume contained, per liter: 2.5 g LB powder, 5 g 4HB as sodium salt, 2 g glucose, 50 mmol potassium phosphate (pH 7), 7 g phosphoric acid, 100 μg ampicillin, and 0.1 mmol IPTG. At this time, the temperature was adjusted to 33° C., and the agitation rate was reduced to 400 rpm. Periodic additions of glucose and sodium 4HB were made when the pH was significantly below or above 7, respectively, because the addition of glucose caused the pH to decrease slowly and the addition of 4HB caused the pH to increase slowly. The pH was not automatically controlled. The fermentation proceeded this way for an additional 70 h, at which time a total of 34 g/L glucose and 15 g/L 4HB had been fed. The cells were allowed to settle at 4° C. for 2 days, after which time the liquid phase was pumped away, and the cell slurry was fluidized in a Microfluidics Corporation (Newton, Mass.) M110-EH Microfluidizer at 18,000 psi. The resulting material was lyophilized and extracted into tetrahydrofuran (THF, 3% wt/vol P4HB) with heating (60° C.) and mechanical stirring. The resulting THF extract was pressure filtered through glass micro-fiber (2.3 μm) and Teflon (2 μm) depth filters. The polymer was precipitated into an equal volume of water and lyophilized. The polymer was redissolved in THF (3% wt/vol P4HB) with heating (60° C.) and the solution was filtered through glass micro-fiber (2.3 μm) and Teflon (2 μm) depth filters and precipitated into water/THF (1:1). The precipitate was washed with water/THF (1:1) and lyophilize to yield a white colored foam (20 g). This material was identified as poly-4-hydroxybutyrate and shown to be non-cytotoxic by an agar diffusion assay (ISO 10993, Toxicon Corp., Bedford, Mass.). Elemental analysis (C 55.63%, H 7.41%, O 37.28%, N 41 ppm). GC analysis shows very low lipids in the purified polymer. NMR analysis shows expected peaks and no lipids.

Example 2

Production of Poly(4HB-co-2HB) in Recombinant *Escherichia coli*

E. coli strains MBX1177/pFS30 and MBX184 (CGSC6966)/pFS30 were precultured in 300 mL LB-ampicillin in a one-liter Erlenmeyer flask at 30° C. overnight with shaking at 200 rpm. Two 100-mL aliquots of each preculture were centrifuged (2000×g, 10 minutes), and the cells obtained from each of these aliquots were resuspended in 100 mL of a medium containing, per liter: 6.25 g LB powder; 2 g glucose; 50 mmol potassium phosphate (pH 7); 100 μg ampicillin; and 100 μmol IPTG. The medium also contained 2-hydroxybutyric acid (2HB) and 4HB; in one flask the concentrations were 8 g/L 2HB and 2 g/L 4HB, and in the other the concentrations of the two acids were each 5 g/L. Both acids were added to the flasks as the sodium salt; the masses given for the acids do not include the mass of sodium. These four flasks (two flasks for each strain) were incubated at 30° C. for an additional 48 hours with shaking at 200 rpm. The cells were removed from the medium by centrifugation (2000×g, 10 minutes), washed once with water, centrifuged again, and lyophilized. Gas chromatographic analysis was carried out on the lyophilized cell mass to analyze for polymer content and composition, see Table 2. The cellular contents and compositions of the PHAs produced are given in Table 2. When the ratio of 2HB to 4HB was 4:1, the 2HB content of the polymer was higher than 19 percent for both strains by GC analysis, while at a 1:1 ratio of 2HB to 4HB, the 2HB content of the polymer was around 1 percent. The 4HB was more readily incorporated into the polymer than was the 2HB; therefore, when 4HB was present at 2 g/L the overall polymer content of the cells is less than when it was present at 5 g/L. The polymers produced by MBX184/pFS30 were extracted from the cells and analyzed. The lyophilized cell mass was incubated in 5 mL of chloroform at 37° C. for 2 hours. The cell debris was removed by centrifugation (2000×g, 5 minutes), and the resulting polymer solution was added dropwise to 50 mL of ethanol to precipitate it. The precipitated polymer was centrifuged from the ethanol as above. In the case of the 4:1 2HB:4HB ratio the polymer was difficult to centrifuge from the ethanol; it formed a haze when added to the ethanol but not nearly all of it could be collected by centrifugation, probably because the molecular weight of this polymer was rather low. The polymer isolated from the 1:1 2HB:4HB flask was easily precipitated from the ethanol, and it was recovered nearly completely. GC analysis of these extracted samples (Table 2) showed that the 2HB content was slightly lower than when the analysis was done on whole cells. It is possible that 2HB residues in the polymer chain are hydrolyzed during the extraction, thus lowering the apparent 2HB content in the extracted samples. The fact that the molecular weight of the extracted polymer was apparently lower when the 2HB content was higher is consistent with this explanation.

A second experiment was performed with MBX184/pFS30. These cells were precultured in 400 mL LB-ampicillin in a one-liter Erlenmeyer flask at 30° C. overnight with shaking at 200 rpm. An addition of 20 ml of medium was made to each flask such that the total volume contained, per liter: 2.5 g additional LB powder; 2 g 4HB as sodium salt; 2 g glucose; 50 mmol potassium phosphate (pH 7); 100 μg ampicillin; 50 μmol IPTG; and 2, 4, 6, or 8 g 2HB as sodium salt. The flasks were incubated for an additional 48 hours at 30° C. and 200 rpm. The cells were removed from the medium by centrifugation (2000×g, 10 minutes), washed once with water, centrifuged again, and lyophilized. The dried cell mass was subjected to GC analysis as above. Table 3 gives the cell content and composition of the polymers thus obtained. At low 2HB:4HB ratios, little or no 2HB was incorporated into the polymer; however, when this ratio was 3:1 or 4:1, 2HB incorporation into the polymer was very significant. The overall polymer content of all the cells was rather low, probably because the acids are not present at concentrations high enough to permit the uptake and/or incorporation to proceed at a high rate.

Example 3

Production of Poly(4HB-co-3HB) in Recombinant E. coli

Strain MBX1177/pFS30 was precultured in 100 ml LB-ampicillin in four separate 250-ml Erlenmeyer flasks at 30° C. overnight with shaking at 200 rpm. An addition of 20 ml of medium was made to each flask such that the total volume contained, per liter: 2.5 g additional LB powder; 4 g 4HB as sodium salt; 4 g glucose; 50 mmol potassium phosphate (pH 7); 100 µg ampicillin; 50 µmol IPTG; and 0.25, 0.5, 0.75, or 1 g 3-hydroxybutyrate (3HB) as sodium salt. The flasks were incubated for an additional 48 hours at 30° C. and 200 rpm. The cells were removed from the medium by centrifugation (2000×g, 10 minutes), washed once with water, centrifuged again, and lyophilized. Gas chromatographic analysis was carried out on the lyophilized cell mass to analyze for polymer content and composition. The standard used to test for 3-hydroxybutyrate units in the polymer was poly(3-hydroxybutyrate). The cellular contents and compositions of the PHAs produced are given in Table 4. As the ratio of 4HB/3HB in the medium decreased, the 3HB content of the polymer increased in a monotonic fashion, while the overall polymer content of the cells was similar in all trials. This means that the composition of the medium can be used predictably to control the copolymer composition without significantly affecting the overall polymer yield. The polymer was extracted from the remainder of the lyophilized cell mass. For all samples, lyophilized cell mass was mixed with about three times its own volume of 1,2-dichloroethane and incubated with mild shaking in a closed tube at 37° C. for 6 hours. The particulate matter was separated from the polymer solution by centrifugation (2000×g, 10 minutes). The resulting solution was added dropwise to about 10 times its own volume of ethanol, and the precipitated polymer was allowed to settle out of solution. The supernatant was poured off, and the remaining wet polymer was allowed to stand until it appeared to be dry, then it was lyophilized to complete dryness. Thermal properties of these P4HB-co-3HB compositions are shown in Table 5.

Example 4

In vitro and in vivo Degradation of P4HB

Figure 3:
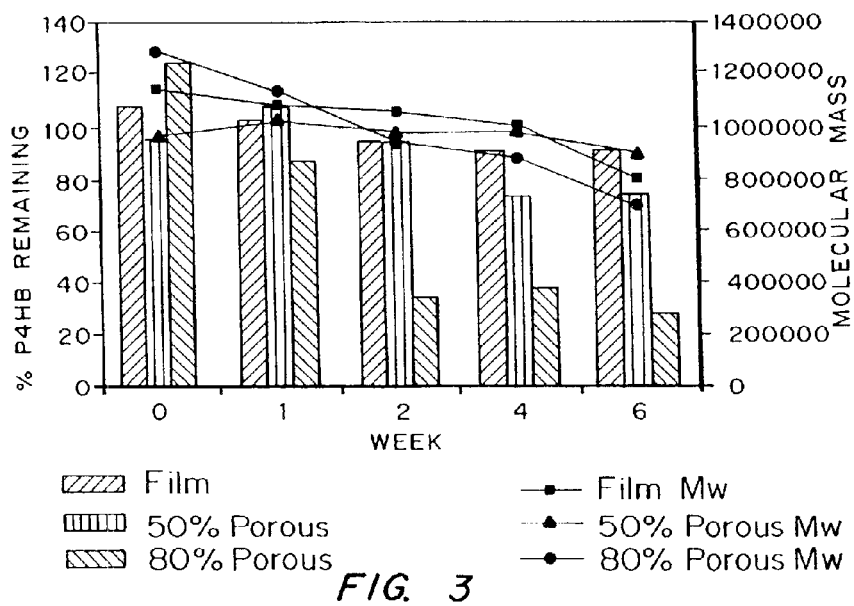
FIG. 3 is a graph of P4HB degradation in vivo over time (weeks).

The degradation of P4HB was studied in vitro and in vivo. Three different configurations of varying porosity (0%, 50% and 80% porosity) were examined. Small disks (5 mm diameter) were punched from compression molded P4HB films of uniform thickness. Porous samples of P4HB were produced using the salt leaching technique described below. The degradation behavior in vitro was studied by incubating the disks in a sterile, phosphate buffer (8 mM sodium phosphate, 2 mM potassium phosphate, 140 MM NaCl, 10 mM KCl, pH 7.4, containing $NaN_3$ as preservative) at 37° C. The degradation behavior in vivo was studied after implantation in subcutaneous pockets in rats.
Preparation of porous P4HB Classified sodium chloride crystals (80–180 µm) were mixed with molten P4HB. The polymer salt ratio can be adjusted to produce the desired porosity, while particle size may be adjusted to produce pores of varying size. The polymer salt mixture was pressed into a thin film. After allowing the material to solidify, the film was removed from the mylar backing. The film was exhaustively extracted with water to remove the salt, leaving a porous film of P4HB.
Accelerated Degradation of P4HB The degradation of P4HB was studied in vivo. Three different configurations of varying porosity (0%, 50% and 80% porosity) were examined. Small disks (5 mm diam.) were punched from compression molded P4HB films of uniform thickness. Porous samples of P4HB were produced using a salt leaching technique. The degradation behavior in vivo was studied after implantation in subcutaneous pockets in rats. Samples were removed at various times. The molecular mass was measured by GPC and mass loss was measured by quantification of the remaining 4HB by CG analysis. The results are shown in FIG. 3. As shown in FIG. 3, the sample mass loss varied with porosity. Film, 50% and 80% porous samples showed a 5%, 20% and 75% mass loss, respectively, over the six week period, while the average molecular mass loss of these samples also decreased significantly (20 to 50%). These data demonstrate that the degradation rate of PHAs can be modified and controlled by altering porosity and increasing surface area.

Results

The P4HB implants showed a very minimal inflammatory response, much less so than for a PGA non-woven mesh. This is a very good indication of the biocompatibility of these materials. Samples were removed at various times and evaluated histologically both as to the implants and surrounding tissue. The molecular mass was measured by GPC and mass loss was measured by quantification of the remaining 4HB by GC analysis. The results are shown in Tables 6 and 7. As shown in Table 6, P4HB does not degrade significantly over a ten week period in vitro. All of the samples maintained their starting weight and there was about a 20 to 40% decrease in average molecular mass. The samples incubated in vivo showed much more pronounced degradation. The mass loss varied with porosity. Film, 50% and 80% porous samples showed a 20%, 50% and 100% mass loss, respectively, over the ten week period, while the average molecular mass loss of these samples also decreased significantly (20 to 50%).

Light microscopic and environmental scanning electron microscopy (ESEM) examination of the samples show almost no discernible change for the in vitro samples over the ten week incubation period. On the other hand, the in vivo implants show distinct signs of degradation. The surface of these materials becomes progressively degraded during the ten week implantation period. After one week, the film samples show some signs of cracking and crazing, which progresses to surface erosion and pitting over the following nine weeks.

The in vitro degradation data suggest that P4HB is fairly stable to simple hydrolysis, unlike other polyesters used in bioresorbable applications, such as PGA, PLA and their copolymers. However, the degradation of the implants indicates that P4HB can be degraded in vivo, suggesting a biologically mediated mode of degradation. The data shows increasing degradation with increasing porosity, which indicates that surface area of the polymer implant plays a role in its degradation in vivo. This suggests that the degradation of P4HB polymers in vivo occurs at the surface of the implant, unlike PGA or PLA materials which degrade throughout the implant by hydrolysis, with associated molecular mass decrease and loss of mechanical properties. These data suggest that the degradation rate of P4HB can be modified and controlled by altering its surface area. Also, it is expected that this type of surface degradation will result in a relatively slow rate of molecular mass loss allowing for the maintenance of polymer material properties longer than existing absorbable, medical polyesters. The P4HB implants were very well tolerated and showed only a very minimal foreign body reaction. These findings show that these materials have significant advantages over existing biomedical polyesters.

Example 5

Compression Molding

P4HB was pressed into a thin film using Carver hydraulic press. The platens were heated to 115° C. P4HB was pressed between two sheets of mylar using metal spacers. Spacer thickness and pressure of the press can be adjusted to control film thickness. The film was removed from the press and allowed to cool at room temperature. After solidifying (within a matter of seconds), the film was easily peeled from the mylar backing material. Mechanical data for this material are shown in Table 1. The rapid solidification of P4HB demonstrates it rapid crystallization.

Example 6

Compression Molding of Porous P4HB

Classified sodium chloride crystals (80–180 $\mu$m) were mixed with molten P4HB as described in Examples 4 and 5. The polymer salt ratio can be adjusted to produce the desired porosity, while particle size may be adjusted to produce pores of varying size. The polymer salt mixture was pressed into a thin film using the conditions described in Example 6. After allowing the material to solidify, the film was removed from the mylar backing. The film was exhaustively extracted with water to remove the salt, leaving a porous film of P4HB. Salt removal was monitored by analysis of chloride in the supernatant and confirmed by elemental analysis of the leached film (less than 0.5% chloride). Mechanical data for 50% and 80% porous P4HB (pP4HB50 and pP4HB80, respectively) are shown in Table 1.

Example 7

Cell Seeding of P4HB Scaffolds

Porous P4HB (as described in Example 6) was sterilized by cold ethylene oxide treatment. It was seeded with ovine vascular cells and cultured in vitro. Preliminary data indicated very good attachment of these cells to the material. This is a further demonstration of the biocompatibility of this material. The number of cells attached to the material can be quantified using an assay for DNA and compared with the standard for tissue engineering scaffolds, PGA mesh.

Example 8

Fiber Orientation

Compression molded strips of P4HB were uniaxially stretched. The sample narrowed and became clear, showing signs of necking. After this stretching process, the polymer appeared stronger and somewhat more flexible, demonstrating uniaxial orientation of the sample.

Example 9

Thermal Phase Separation Method for Production of P4HB Foam

P4HB was dissolved in dioxane at 1 to 5% wt./vol. This polymer solution was cast as a thick film and solidified by cooling on ice below the melting point of dioxane. The solvent was evaporated from this solid material at low pressure to yield a porous foam with the approximate dimensions of the starting thick film. ESEM analysis of this material showed a highly porous, sponge-like structure. The polymer concentration and cooling process can be varied to alter the porosity of the foam. Prior to freezing, the polymer solution can be shaped into a variety of forms, broken up into particulate material or used as a coating. Therefore, this thermal phase separation technique can be used to produce a great variety of highly porous, 3-dimensional shapes of P4HB.

Example 10

P4HB Coating of a PGA Non-Woven Mesh

P4HB was dissolved in tetrahydrofuran at 1% wt/vol. A 1 mm thick non-woven mesh of PGA (Albany International, bulk density 52 mg/cc) was dipped into this solution so that the air voids were eliminated. The coated mesh was allowed to air dry and the coating procedure was repeated. Light microscopic and ESEM analyses of the coated mesh showed that during the drying process the polymer migrated to the fiber intersections, and functioned to bind the fibers together. This fiber bonding technique was found to dramatically improve the strength and handleability of the PGA mesh. Tensile testing according to ASTM D638, showed that the tensile strength, Young's modulus and ultimate elongation of this material were 130 psi, 240 psi and 171%. This was a dramatic improvement over the uncoated material which was too fragile to test these parameters.

Example 11

P4HB Foam Coating of a PGA Non-Woven Mesh

P4HB was dissolved in dioxane at 2.5% wt/vol. A 1 mm thick non-woven mesh of PGA (Albany International, bulk density 52 mg/cc) was dipped into this solution so that the air voids were eliminated. The coated mesh was cooled on ice so that the coating solution solidified. The mesh was freeze-dried to remove the dioxane. Light microscopic analysis of the coated mesh showed that during the freeze-drying process the polymer formed a web-like foam throughout the PGA mesh. This foamed material has good handleability. The high surface area and improved mechanical properties are attractive for a variety of applications.

Example 12

Formation of P4HB Microspheres

P4HB was dissolved in dichloromethane at 1% wt/vol. A 1 ml volume of this solution was mixed with 5 ml of a 0.5% wt/vol. solution of sodium dodecylsufate (SDS). The two phase mixture was mechanically mixed to yield an emulsion. A stream of nitrogen was bubbled through the mixture for 1 hour with rapid stirring to facilitate removal of the dichloromethane. The mixture was stirred open to the air overnight to allow for the complete removal of dichloromethane. The resultant suspension contained P4HB microspheres of about 1–10 $\mu$m, as determined under a phase contrast optical microscope.

Summary

Polyhydroxyalkanoates such as the homopolymer P4HB and copolymers containing 4HB have physical properties and degradation characteristics which make them very attractive as implants for use in medical applications. These polymers can be fabricated into fibers, sheets, foams, coating, structures, filaments and the like for use of these as implantable medical materials.

TABLE 1

Thermal and Mechanical Properties of Selected Medical Polymers.

| Polymer | Tm (° C.) | Tg (° C.) | Tensile Str. (psi) | Modulus (psi) | Elongation (%) | Degradation |
|---|---|---|---|---|---|---|
| [1]P4HB | 60 | −51 | 7,500 | 9,400 | 1000 | depends on config. |
| [1]pP4HB50[a] | 60 | −51 | 895 | 2155 | 164 | depends on config. |
| [1]pP4HB80[b] | 60 | −51 | 180 | 257 | 100 | depends on config. |
| [6]P4HB-3HB 10% | 50 | −42 | 9,000 | 14,500 | 1080 | Not reported |
| [1]PHB | 175 | 0 | 4,000 | 110,000 | 4 | >52 wks |
| [2]PGA | 230 | 35 | 10,000 | 1,000,000 | 17 | 8 wks |
| [3]PDLLA | Am | 53 | 5,000 | 300,000 | 5 | <8 wks |
| [3]PLLA | 175 | 55 | 10,000 | 500,000 | 8 | >8 wks |
| [2]DLPLG 50/50 | Am | 48 | 7,000 | 300,000 | 5 | 3–8 wks |
| [5]LDPE | | | 2,000 | | 400–700 | Nondegradable |
| [5]HDPE | | | 4,000 | | 100–1000 | Nondegradable |
| [5]UHMWPE | | | 7,250 | | 450 | Nondegradable |
| PP | | | 4,000 | 20,000 | 200–700 | Nondegradable |
| PET | | | 8,500 | | 50 | Nondegradable |
| PTFE | | | 3,000 @ Yield | 50,000 | 300 | Nondegradable |

[a]pP4HB50, 50% porous P4HB, see example 7.
[b]pP4HB80, 80% porous P4HB, see example 7.
Ref:
[1]From this work measured according to ASTMD638 at ambient temperature and a strain rate of 0.05 or 0.1 in./min..
[2]Hutmacher et al. Int. J. Oral Max. Imp. 1996, 11, 667–678.
[3]Nobes et al. submitted.
[4]Mark, Physical Properties of Polymers Handbook, American Inst. of Physics, Woodbury, New York, 1996.
[5]Schwartz, S. S. and Goodman, S. H. Plastic Materials and Processes, Van Nostrand Reinhold Company, New York, 1982.
[6]Saito, Y. and Doi, Y. Int. J. Biol. Macromol. (1994) 16: 99–104.

TABLE 2

GC analysis of poly(4HB-co-2HB) from MBX1177/pFS30 and MBX184/pFS30.

| Strain | 4HB, g/L | 2HB, g/L | Total PHA, % of dcw[a] | P4HB, % of PHA[b] | P2HB, % of PHA[b] |
|---|---|---|---|---|---|
| 184/30 | 2 | 8 | 18.3 | 70.8 | 19.2 (14.2)[c] |
| 184/30 | 5 | 5 | 47.1 | 98.8 | 1.2 (0.9)[c] |
| 1177/30 | 2 | 8 | 13.0 | 62.3 | 27.7 |
| 1177/30 | 5 | 5 | 40.1 | 98.9 | 1.1 |

[a]dcw: dry cell weight.
[b]Determined by GC analysis. About 20 mg of lyophilized cell mass was subjected to butanolysis at 110° C. for 3 hours in 2 mL of a mixture containing (by volume) 90% 1-butanol and 10% concentrated hydrochloric acid, with 2 mg/mL benzoic acid added as an internal standard. The water-soluble components of the resulting mixture were removed by extraction with 3 mL water. The organic phase (1 μL at a split ratio of 1:50 at an overall flow rate of 2 mL/min) was analyzed on an SPB-1 fused silica capillary GC colum (30 m; 0.32 mm ID; 0.25 μm film; Supelco; Bellefonte, Pa.) with the following temperature profile: 80° C., 2 min.; 10 C. ° per min. to 250° C.; 250° C., 2 min. The standard used to test for the presence of 4-hydroxybutyrate units in the polymer was γ-butyrolactone. The standard used to test for 2-hydroxybutyrate units in the polymer was sodium (2-hydroxybutyrate).
[c]Percentages in parentheses were determined by GC analysis as above, but after extraction of the polymer into chloroform and subsequent precipitation in ethanol.

TABLE 3

GC analysis of poly(4HB-co-2HB) from MBX184/pFS30.

| Sample | 4HB, g/L | 2HB, g/L | Total PHA, % of dcw[a] | P4HB, % of PHA[b] | P2HB, % of PHA[b] |
|---|---|---|---|---|---|
| 1 | 2 | 2 | 8.2 | 100 | 0 |
| 2 | 2 | 4 | 5.6 | 100 | 0 |
| 3 | 2 | 6 | 5.7 | 84.1 | 15.9 |
| 4 | 2 | 8 | 4.1 | 54.3 | 45.7 |

[a]dcw: dry cell weight.
[b]Determined by GC analysis. See Table 2 for details.

TABLE 4

GC analysis of poly(4HB-co-3HB) from MBX1177/pFS30.

| Sample | 4HB, g/L | 3HB, g/L | Total PHA, % of dcw[a] | P4HB, % of PHA[b] | P3HB, % of PHA[b] |
|---|---|---|---|---|---|
| 3a | 4 | 0.25 | 49.3 | 98.0 | 2.0 |
| 3b | 4 | 0.5 | 46.7 | 94.2 | 5.8 |
| 3c | 4 | 0.75 | 56.6 | 91.7 | 8.3 |
| 3d | 4 | 1 | 51.8 | 89.4 | 10.6 |

[a]dcw: dry cell weight.
[b]Determined by GC analysis. See Table 2 for details. The standard used to test for the presence of 4-hydroxybutyrate units in the polymer was γ-butyrolactone. The standard used to test for 3-hydroxybutyrate units in the polymer was poly(3-hydroxybutyrate).

TABLE 5

Properties of P4HB and P4HB-co-3HB from MBX1177/pFS30.

| Sample | %[a] 4HB | %[a] 3HB | Tm[b] (° C.) | dH Tm1[b] (J/g) | Tg[b] (° C.) | Tx[b] (° C.) | Tm2[b] (° C.) | Mw[c] |
|---|---|---|---|---|---|---|---|---|
| P4HB | 100 | 0 | 60 | 45 | −51 | −16 | X | 1,000,000 |
| 3b | 94.2 | 5.8 | 47 | 36 | −52 | −4 | 44 | 1,500,000 |
| 3c | 91.7 | 8.3 | 40 | 20 | −53 | nd | 39 | 1,900,000 |
| 3d | 89.4 | 10.6 | 39 | 17 | −53 | nd | nd | 1,100,000 | nd—not detected.
[a]Determined by GC analysis, see Table 2 for details.
[b]Determined by DSC analysis. A Perkin Elmer Pyris 1 differential scanning calorimeter was used. Samples masses were approximately 4–8 mg. The thermal program used was as follows: 25° C., 2 min.; heat to 195° C. at 10 C. ° per min.; hold at 195° C. 2 min.; cool to −80° C. at 300 C. ° per min.; hold at −80° C. for 2 min.; heat to 195° C. at 10 C. ° per min. The melting temperature (Tm) and the enthalpy of fusion of this melting peak (dHTm1) were determined in the first heating cycle. Glass transition temperature (Tg), crystallization temperature (Tx) and melting temperature (Tm2) were determined during the second heating cycle. [c]Determined by GPC analysis. Isolated polymers were dissolved in chloroform at approximately 1 mg/mL and samples (50 μL) were chromatographed on a Waters Stryagel HT6E column at a flow rate of 1 mL chloroform per minute at room temperature using a refractive index detector. Molecular masses were determined relative to polystyrene standards of narrow polydispersity.

TABLE 6

Degradation of P4HB in vitro. Percent original mass remaining and molecular mass of film, 50% porous and 80% porous samples of P4HB incubated in phosphate buffer (8 mM sodium phosphate, 2 mM potassium phosphate, 140 mM NaCl, 10 mM KCl, pH 7.4, containing NaN₃ as preservative) at 37° C..

| Implantation (weeks) | Film Weight % Remaining[a] | Film Molecular Mass[b] | 50% Por. Weight % Remaining[a] | 50% Por. Molecular Mass[b] | 80% Por. Weight % Remaining[a] | 80% Por. Molecular Mass[b] |
|---|---|---|---|---|---|---|
| 0 | 108 | 1144592 | 96 | 963145 | 123 | 1291117 |
| 1 | 97 | 1160707 | 93 | 1103860 | 99 | 968245 |
| 2 | 101 | 1008496 | 98 | 1055614 | 106 | 1072328 |
| 4 | 100 | 887005 | 96 | 725089 | 116 | 987665 |
| 6 | 109 | 896521 | 97 | 764260 | 95 | 1049079 |
| 10 | 92 | 772485 | 90 | 605608 | 100 | 727543 |

[a]Determined by GPC analysis. See Table 3 for details.
[b]Determined by quantitative GC analysis. See Table 2 for details.

TABLE 7

Degradation of P4HB in vivo. Percent original mass remaining and molecular mass of film, 50% porous and 80% porous samples of P4HB implanted subcutaneously in rats.

| Implantation (weeks) | Film Weight % Remaining[a] | Film Molecular Mass[b] | 50% Por. Weight % Remaining[a] | 50% Por. Molecular Mass[b] | 80% Por. Weight % Remaining[a] | 80% Por. Molecular Mass[b] |
|---|---|---|---|---|---|---|
| 0 | 108 | 1144592 | 96 | 963145 | 123 | 1291117 |
| 1 | 103 | 1091107 | 109 | 1026821 | 88 | 1132492 |
| 2 | 95 | 1054873 | 94 | 973830 | 35 | 943960 |
| 4 | 92 | 1007736 | 73 | 989629 | 39 | 881919 |
| 6 | 90 | 797170 | 74 | 901330 | 28 | 689157 |
| 10 | 80 | 716296 | 48 | 647175 | 0 | N/D |

N/D Not determined.
[a]Determined by GPC analysis. See Table 3 for details.
[b]Determined by GC analysis. See Table 2 for details. Explants often weighed more than the original implant due to the presence of adherent tissue or coagulated blood. Therefore, the mass of P4HB in the explant was determined by quantitative GC analysis. Weight percent remaining P4HB was taken as this mass divided by original implant.

We claim:

1. A method for preparing a biocompatible biodegradable polyhydroxyalkanoate composition that has a controlled degradation rate under physiological conditions, wherein the mass loss, as measured bvxas chromatography, is greater than 5% over a six week period in vivo, or wherein the average molecular mass loss, as measured by gel permeation chromatography, decreases 20% to 50% over a ten week period in vivo, comprising (a) incorporating monomeric units as chemical linkages into the polymer backbone which alter the chemical stability of the polymer backbone;

(b) replacing linkages in said polymer backbone which alter the chemical stability of the polymer backbone;

(c) incorporating pendant groups into the polymer which alter the chemical stability of the polymer backbone;

(d) incorporating additives which alter the chemical stability of the polymer; or (e) combinations thereof.

2. The method of claim 1 further comprising forming the polyhydroxyalkanoate composition using a method selected from the group consisting of fermentation, enzymatic synthesis, chemical synthesis, melt processing, reactive blending, and recombinant techniques.

3. The method of claim 2 wherein the composition is derived by fermentation using a co-feed.

4. The method of claim 2 wherein the fermentation process uses transgenic bacteria.

5. The method of claim 2 wherein the chemical synthesis is selected from the group consisting of insertion, transesterification and metathesis.

6. The method of claim 1 wherein the presence of the additional unit(s) promotes chain scission.

7. The method of claim 1 wherein the units contain more than two functional groups.

8. The method of claim 1 wherein a heteroatom grouping is incorporated into the polymer backbone chain.

9. The method of claim 8 wherein the heteroatom grouping is selected from the group consisting of oxygen, sulfur and nitrogen.

10. The method of claim 1 wherein the units are incorporated into the polymer backbone with chemical linkages selected from the group consisting of ester, amide, ether, carbamate, anhydride, and carbonate.

11. The method of claim 1 wherein the units are selected from the group consisting of 2-hydroxyacids; 2-hydroxyalkoxyacetic acids; amino acids; amino alcohols; diacids; triols; and tetraols.

12. The method of claim 11 wherein the 2-hydroxyacids are 2-hydroxyalkanoic acids.

13. The method of claim 12 wherein the 2-hydroxyalkanoic acid is lactic acid.

14. The method of claim 12 wherein the 2-hydroxyalkanoic acid is glycolic acid.

15. The method of claim 11 wherein the 2-hydroxyacids are 2-hydroxyalkenoic acids.

16. The method of claim 11 wherein the 2-hydroxyalkoxyacetic acids are selected from the group consisting of 2-hydroxyethoxy acetic acid and 3-hydroxypropoxy acetic acid.

17. The method of claim 1 comprising pendant groups that catalyze the degradation of the polymer backbone.

18. The method of claim 17 wherein the pendant groups are selected from acidic and basic groups.

19. The method of claim 17 comprising reactant pendant groups that cause polymer chain scission.

20. The method of claim 19 wherein the reactant pendant groups are selected from nucleophiles and electrophiles.

21. The method of claim 17 wherein the pendant groups are selected from the group consisting of alcohols, acids and amine groups.

22. The method of claim 1 wherein the additives promote chain scission.

23. The method of claim 22 wherein the additives are selected from the group consisting of acids, bases, electrophiles, nucleophiles, plasticizers, polymers, pore forming agents, and agents designed to reduce the polymer crystallinity.

24. The method of claim 23 comprising pore forming agents.

25. The method of claim 24 wherein the pore forming agents are lyophilizable particles.

26. The method of claim 24 wherein the pore forming agents absorb water.

* * * * *

UNITED STATES PATENT AND TRADEMARK OFFICE
CERTIFICATE OF CORRECTION

PATENT NO. : 6,878,758 B2
APPLICATION NO. : 10/403942
DATED : April 12, 2005
INVENTOR(S) : David P. Martin, Frank Skraly and Simon F. Williams It is certified that error appears in the above-identified patent and that said Letters Patent is hereby corrected as shown below:

Claim 1, column 25, line 5, replace "bvxas" with --by gas--.

Signed and Sealed this

Nineteenth Day of June, 2007

JON W. DUDAS
*Director of the United States Patent and Trademark Office*